(12) United States Patent
Siejko et al.

(10) Patent No.: US 7,123,962 B2
(45) Date of Patent: Oct. 17, 2006

(54) PHONOCARDIOGRAPHIC IMAGE-BASED ATRIOVENTRICULAR DELAY OPTIMIZATION

(75) Inventors: Krzysztof Z. Siejko, Maple Grove, MN (US); Gerrard M. Carlson, Champlin, MN (US); William C. Lincoln, Coon Rapids, MN (US); Andrew P. Kramer, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 641 days.

(21) Appl. No.: 10/307,896

(22) Filed: Dec. 2, 2002

(65) Prior Publication Data

US 2004/0106960 A1    Jun. 3, 2004

(51) Int. Cl.
*A61N 1/365* (2006.01)
(52) U.S. Cl. ........................... 607/17; 607/18
(58) Field of Classification Search .................. 607/4, 607/9, 17–18, 30–33
See application file for complete search history.

(56) References Cited

U.S. PATENT DOCUMENTS

| | | |
|---|---|---|
| 4,428,380 A | 1/1984 | Wong et al. |
| 4,628,939 A | 12/1986 | Little et al. |
| 4,763,646 A | 8/1988 | Lekholm |
| 4,905,706 A | 3/1990 | Duff et al. |
| 4,922,907 A | 5/1990 | Hedin et al. |
| 4,967,760 A | 11/1990 | Bennett et al. |
| 4,981,139 A | 1/1991 | Pfohl |
| 5,025,809 A | 6/1991 | Johnson et al. |
| 5,168,869 A | 12/1992 | Chirife |
| 5,179,947 A | 1/1993 | Meyerson et al. |
| 5,301,679 A | 4/1994 | Taylor |
| 5,318,595 A | 6/1994 | Ferek-Petric et al. |
| 5,330,511 A | 7/1994 | Boute |
| 5,337,752 A | 8/1994 | Reeves |
| 5,514,163 A | 5/1996 | Markowitz et al. |
| 5,527,347 A | 6/1996 | Shelton et al. |
| 5,549,650 A | 8/1996 | Bornzin et al. |
| 5,554,177 A * | 9/1996 | Kieval et al. .................. 607/17 |
| 5,609,612 A | 3/1997 | Plicchi et al. |
| 5,626,620 A | 5/1997 | Kieval et al. |

(Continued)

FOREIGN PATENT DOCUMENTS

EP    0474958    3/1992

(Continued)

OTHER PUBLICATIONS

Kinderman, Michael et al., "Optimizing the AV Delay in DDD Pacemaker Patients with High Degree AV Block: Mitral Valve Doppler Versus Impedance Cardiography", *Pace*, vol. 20, pp. 2453-2462, (Oct. 1997).

(Continued)

*Primary Examiner*—Carl Layno
(74) *Attorney, Agent, or Firm*—Schwegman, Lundberg, Woessner, & Kluth, P.A.

(57) ABSTRACT

A cardiac rhythm management system provides a phonocardiographic image indicative of a heart's mechanical events related to hemodynamic performance to allow, among other things, diagnosis of cardiac conditions and evaluation of therapies treating the cardiac conditions. The phonocardiographic image includes a stack of acoustic sensor signal segments representing multiple cardiac cycles. Each acoustic sensor signal segment includes heart sounds indicative of the heart's mechanical events and representations of the heart's electrical events. The diagnosis and/or therapy evaluation are performed by observing or detecting at least an occurrence of a particular heart sound related to a cardiac time interval or a trend of a particular time interval between an electrical event and a mechanical event over the cardiac time interval.

45 Claims, 14 Drawing Sheets

U.S. PATENT DOCUMENTS

| | | | |
|---|---|---|---|
| 5,626,623 A | 5/1997 | Kieval et al. | |
| 5,628,777 A | 5/1997 | Moberg et al. | |
| 5,674,256 A | 10/1997 | Carlson | 607/17 |
| 5,687,738 A | 11/1997 | Shapiro et al. | |
| 5,690,689 A | 11/1997 | Sholder | |
| 5,700,283 A | 12/1997 | Salo | 607/17 |
| 5,713,930 A | 2/1998 | van der Veen et al. | |
| 5,716,383 A | 2/1998 | Kieval et al. | |
| 5,749,906 A | 5/1998 | Kieval et al. | |
| 5,792,195 A * | 8/1998 | Carlson et al. | 607/17 |
| 5,800,471 A | 9/1998 | Baumann | |
| 5,836,987 A * | 11/1998 | Baumann et al. | 607/17 |
| 5,860,933 A | 1/1999 | Don Michael | |
| 5,935,081 A | 8/1999 | Kadhiresan | |
| 6,044,298 A | 3/2000 | Salo et al. | 607/17 |
| 6,044,299 A | 3/2000 | Nilsson | |
| 6,058,329 A | 5/2000 | Salo et al. | 607/17 |
| 6,144,880 A | 11/2000 | Ding et al. | 607/23 |
| 6,193,668 B1 | 2/2001 | Chassaing et al. | |
| 6,208,901 B1 | 3/2001 | Hartung | |
| 6,272,377 B1 | 8/2001 | Sweeney et al. | |
| 6,280,389 B1 | 8/2001 | Ding et al. | |
| 6,311,089 B1 | 10/2001 | Mann et al. | |
| 6,351,673 B1 | 2/2002 | Ding et al. | 607/24 |
| 6,360,127 B1 | 3/2002 | Ding et al. | 607/23 |
| 6,366,811 B1 | 4/2002 | Carlson | |
| 6,409,675 B1 | 6/2002 | Turcott | |
| 6,430,439 B1 | 8/2002 | Wentkowski et al. | |
| 6,438,421 B1 | 8/2002 | Stahmann et al. | |
| 6,449,510 B1 | 9/2002 | Albers et al. | |
| 6,477,406 B1 | 11/2002 | Turcott | |
| 6,478,746 B1 | 11/2002 | Chassaing et al. | |
| 6,480,733 B1 | 11/2002 | Turcott | |
| 6,480,742 B1 | 11/2002 | Stahmann et al. | |
| 6,491,639 B1 | 12/2002 | Turcott | |
| 6,507,756 B1 | 1/2003 | Heynen et al. | |
| 6,512,952 B1 | 1/2003 | Stahmann et al. | |
| 6,520,924 B1 | 2/2003 | Lee | |
| 6,522,921 B1 | 2/2003 | Stahmann et al. | |
| 6,522,923 B1 | 2/2003 | Turcott | |
| 6,527,729 B1 | 3/2003 | Turcott | |
| 6,542,775 B1 | 4/2003 | Ding et al. | |
| 6,553,258 B1 | 4/2003 | Stahmann et al. | |
| 6,575,916 B1 | 6/2003 | Halleck et al. | |
| 6,626,842 B1 | 9/2003 | Oka | |
| 6,643,548 B1 * | 11/2003 | Mai et al. | 607/17 |
| 6,665,564 B1 * | 12/2003 | Lincoln et al. | 607/17 |
| 6,684,103 B1 | 1/2004 | Ding et al. | |
| 6,792,308 B1 * | 9/2004 | Corbucci | 607/17 |
| 6,810,287 B1 * | 10/2004 | Zhu et al. | 607/17 |
| 2002/0151938 A1 | 10/2002 | Corbucci | |
| 2003/0078624 A1 | 4/2003 | Carlson et al. | |
| 2003/0105496 A1 | 6/2003 | Yu et al. | |
| 2003/0144702 A1 | 7/2003 | Yu et al. | |
| 2003/0144703 A1 | 7/2003 | Yu et al. | |
| 2003/0208240 A1 * | 11/2003 | Pastore et al. | 607/17 |
| 2004/0024423 A1 | 2/2004 | Lincoln et al. | |
| 2004/0078059 A1 | 4/2004 | Ding et al. | |
| 2004/0078060 A1 | 4/2004 | Ding et al. | |
| 2004/0106960 A1 | 6/2004 | Siejko et al. | |
| 2004/0106961 A1 | 6/2004 | Siejko et al. | |
| 2004/0122484 A1 | 6/2004 | Hatlestad et al. | |
| 2004/0127792 A1 | 7/2004 | Siejko et al. | |
| 2005/0102001 A1 | 5/2005 | Maile et al. | |
| 2005/0148896 A1 | 7/2005 | Siejko et al. | |
| 2005/0149136 A1 | 7/2005 | Siejko et al. | |

FOREIGN PATENT DOCUMENTS

| | | |
|---|---|---|
| WO | WO-0156651 A1 | 8/2001 |
| WO | WO-04/060483 A1 | 7/2004 |
| WO | WO-04/60483 A1 | 7/2004 |
| WO | WO-2005122902 A1 | 12/2005 |

OTHER PUBLICATIONS

Leonelli, Fabio M. et al., "Systolic and Diastolic Effects of Variable Atroventricular Delay and Patients with Complete Hear Block and Normal Ventricular Function", *Amer. J-Cardiology*, vol. 80, pp. 294-298, (Aug. 1, 1997).

Phillippe, Ritter et al. ,"New Method for Determining the Optimal Atrio-Ventricular Delay ini Patients Place in DDD Mode for Complete Atrio-Ventricular Block", *NASPE abstract #237*, p. 885, (1995).

Brockway, Marina, et al., "Method and Apparatus for Monitoring Heart Failure Patients With Cardiopulmonary Comorbidities", U.S. Appl. No. 10/897,856, filed Jul. 23, 2004, 54 pages.

Brockway, Marina, et al., "Method and Apparatus for Optimization of Cardiac Resynchronization Therapy Using Heart Sounds", U.S. Appl. No. 10/865,498, filed Jun. 10, 2004, 45 pgs.

Maile, Keith R., et al., "Determining a Patient's Posture From Mechanical Vibrations of the Heart", U.S. Appl. No., 10/900,570, filed Jul. 28, 2004, 24 pgs.

Ritter, P., et al., "A Built-In System Based on the Peak Endocardial Acceleration (PEA) for AV-Delay Optimization in DDDR Pacing", PACE, 20(5) (Part II), (Abstract of Paper presented at EUROPACE '97),(May 1997), p. 1567.

Siejko, K. Z., et al., "Method for Correction of Posture Dependence on Heart Sounds", U.S. Appl. No. 11/037,275, filed Jan. 18, 2005, 26 pgs.

Wariar, R., et al., "Systems and Methods for Multi-Axis Cardiac Vibration Measurments", U.S. Appl. No. 11/135,985, filed May 24, 2004.

Zhang, Y., et al., "Ischemia Detection Using a Heart Sound Sensor", U.S. Appl. No. 11/148,107, filed Jun. 8, 2005, 41 pgs.

\* cited by examiner

PHONOCARDIOGRAPHIC IMAGE-BASED ATRIOVENTRICULAR DELAY OPTIMIZATION

CROSS-REFERENCE TO RELATED APPLICATION(S)

This application is related to co-pending, commonly assigned Siejko et al. U.S. patent application Ser. No. 10/307,900, entitled "METHOD AND APPARATUS FOR PHONOCARDIOGRAPHIC IMAGE ACQUISITION AND PRESENTATION," filed on even date herewith, which is hereby incorporated by reference.

TECHNICAL FIELD

This document relates generally to cardiac rhythm management systems and particularly, but not by way of limitation, to such a system providing for phonocardiographic image-based diagnosis and therapy evaluation.

BACKGROUND

A heart is the center of a person's circulatory system. It includes a complex electromechanical system performing two major pumping functions. The left portions of the heart, including the left atrium and the left ventricle, draw oxygenated blood from the lungs and pump it to the organs of the body to provide the organs with their metabolic needs for oxygen. The right portions of the heart, including the right atrium and the right ventricle, draw deoxygenated blood from the organs and pump it into the lungs where the blood gets oxygenated. These mechanical pumping functions are accomplished by contractions of the myocardium (heart muscles). In a normal heart, the sinus node, the heart's natural pacemaker, generates electrical signals, called action potentials, that propagate through an electrical conduction system to various regions of the heart to excite myocardial tissues in these regions. Coordinated delays in the propagations of the action potentials in a normal electrical conduction system cause the various regions of the heart to contract in synchrony to such that the pumping functions are performed efficiently. Thus, the normal pumping functions of the heart, indicated by hemodynamic performance, require a normal electrical system to generate the action potentials and deliver them to designated portions of the myocardium with proper timing, a normal myocardium capable of contracting with sufficient strength, and a normal electromechanical association such that all regions of the heart are excitable by the action potentials.

The function of the electrical system is indicated by electrocardiography (ECG) with at least two electrodes placed in or about the heart to sense the action potentials. When the heart functions irregularly or abnormally, one or more ECG signals indicate that contractions at various cardiac regions are chaotic and unsynchronized. Such conditions, which are related to irregular or other abnormal cardiac rhythms, are known as cardiac arrhythmias. Cardiac arrhythmias result in a reduced pumping efficiency of the heart, and hence, diminished blood circulation. Examples of such arrhythmias include bradyarrhythmias, that is, hearts that beat too slowly or irregularly, and tachyarrhythmias, that is, hearts that beat too quickly. A patient may also suffer from weakened contraction strength related to deterioration of the myocardium. This further reduces the pumping efficiency. For example, a heart failure patient suffers from an abnormal electrical conduction system with excessive conduction delays and deteriorated heart muscles that result in asynchronous and weak heart contractions, and hence, reduced pumping efficiency, or poor hemodynamic performance.

A cardiac rhythm management system includes a cardiac rhythm management device used to restore the heart's pumping function, or hemodynamic performance. Cardiac rhythm management devices include, among other things, pacemakers, also referred to as pacers. Pacemakers are often used to treat patients with bradyarrhythmias. Such pacemakers may coordinate atrial and ventricular contractions to improve the heart's pumping efficiency. Cardiac rhythm management devices also include defibrillators that deliver higher energy electrical stimuli to the heart. Such defibrillators may also include cardioverters, which synchronize the delivery of such stimuli to portions of sensed intrinsic heart activity signals. Defibrillators are often used to treat patients with tachyarrhythmias. In addition to pacemakers and defibrillators, cardiac rhythm management devices also include, among other things, devices that combine the functions of pacemakers and defibrillators, drug delivery devices, and any other devices for diagnosing or treating cardiac arrhythmias. Efficacy of a cardiac rhythm management therapy is measured by its ability to restore the heart's pumping efficiency, or the hemodynamic performance, which depends on the conditions of the heart's electrical system, the myocardium, and the electromechanical association. Therefore, in addition to the ECG indicative of activities of the heart's electrical system, there is a need to measure the heart's mechanical activities indicative of the hemodynamic performance in response to the therapy, especially when the patient suffers from a deteriorated myocardium and/or poor electromechanical association.

For these and other reasons, there is a need for evaluating therapies by monitoring both electrical and mechanical activities of the heart.

SUMMARY

A cardiac rhythm management system provides a phonocardiographic image indicative of a heart's mechanical events related to hemodynamic performance to allow, among other things, diagnosis of cardiac conditions and evaluation of therapies treating the cardiac conditions. The phonocardiographic image includes a stack of acoustic sensor signal segments representing multiple cardiac cycles. Each acoustic sensor signal segment includes indications of heart sounds related to the heart's mechanical events and representations of the heart's electrical events. The diagnosis and/or therapy evaluation are performed by observing or detecting at least an occurrence of a particular heart sound related to a cardiac time interval or a trend of a particular time interval between an electrical event and a mechanical event over the cardiac time interval.

In one embodiment, a system includes a sensing circuit, a therapy circuit, an acoustic sensor, a controller, and a processor. The sensing circuit senses a cardiac signal. The therapy circuit delivers pacing pulses. The acoustic sensor produces an acoustic sensor signal indicative of heart sounds. The controller includes a therapy protocol synthesizer and an automatic therapy protocol execution module. The therapy protocol synthesizer generates a sequence of pacing parameters. The automatic therapy protocol execution module times pacing pulse deliveries each associated with one of the sequence of pacing parameters. The processor includes an image formation module. The image formation module produces a phonocardiographic image based on the cardiac signal and the acoustic sensor signal. The phonocardiographic image including a stack of segments of the acoustic sensor signal aligned by a selected type of the cardiac events and grouped by at the sequence of pacing parameters.

In one embodiment, a cardiac rhythm management system includes an implantable device, an acoustic sensor, and an external programmer. The implantable device includes a sensing circuit and a therapy circuit. The sensing circuit senses a cardiac signal. The therapy circuit delivers pacing pulses. The acoustic sensor produces an acoustic sensor signal indicative of heart sounds. The external programmer includes a controller and a processor. The controller includes a therapy protocol synthesizer and an automatic therapy protocol execution module. The therapy protocol synthesizer generates a sequence of pacing parameters. The automatic therapy protocol execution module times deliveries of pacing therapies each using one of the sequence of pacing parameters. The processor includes an image formation module that produces the phonocardiographic image.

In one embodiment, a sequence of atrioventricular delays (AVDs) are generated. A sequence of pacing pulses, each associated with one of the AVDs, is delivered. A cardiac signal and an acoustic sensor signal are received to indicate cardiac events and heart sounds, respectively, during the delivering the first sequence of pacing therapies. The phonocardiographic image is formed based on the cardiac signal and the acoustic sensor signal. The phonocardiographic image includes a stack of segments of the acoustic sensor signal aligned by a selected type of the cardiac events and grouped by at least the sequence of AVDs.

In one embodiment, a cardiac signal and an acoustic sensor signal are received. The cardiac signal indicates at least atrial contractions. The acoustic sensor signal indicates heart sounds associated with intrinsic and paced ventricular contractions. Time intervals are measured between an atrial contraction and a heart sound associated with an intrinsic ventricular contraction and between another atrial contraction and a heart sound associated with a paced ventricular contraction. An approximately optimal pacing therapy is determined based on the measured time intervals.

BRIEF DESCRIPTION OF THE DRAWINGS

In the drawings, which are not necessarily drawn to scale, like numerals describe similar components throughout the several views. Like numerals having different letter suffixes represent different instances of similar components. The drawings illustrate generally, by way of example, but not by way of limitation, various embodiments discussed in the present document.

DETAILED DESCRIPTION

In the following detailed description, reference is made to the accompanying drawings that form a part hereof, and in which is shown, by way of illustration, specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not to be taken in a limiting sense, and the scope of the present invention is defined by the appended claims and their equivalents.

This document discusses, among other things, a phonocardiographic image indicative of a heart's mechanical events related to the heart's pumping functions and hemodynamic performance to allow, among other things, diagnosis of cardiac conditions and evaluation of therapies treating the cardiac conditions. The present method and apparatus will be described in applications involving implantable cardiac rhythm management systems such as systems including pacemakers, cardioverter/defibrillators, pacer/defibrillators, and cardiac resynchronization therapy (CRT) devices. However, it is to be understood that the present methods and apparatuses may be employed in other types of medical devices, including, but not being limited to, external cardiac rhythm management systems, drug delivery systems, and various types of cardiac monitoring devices.

Figure 1:
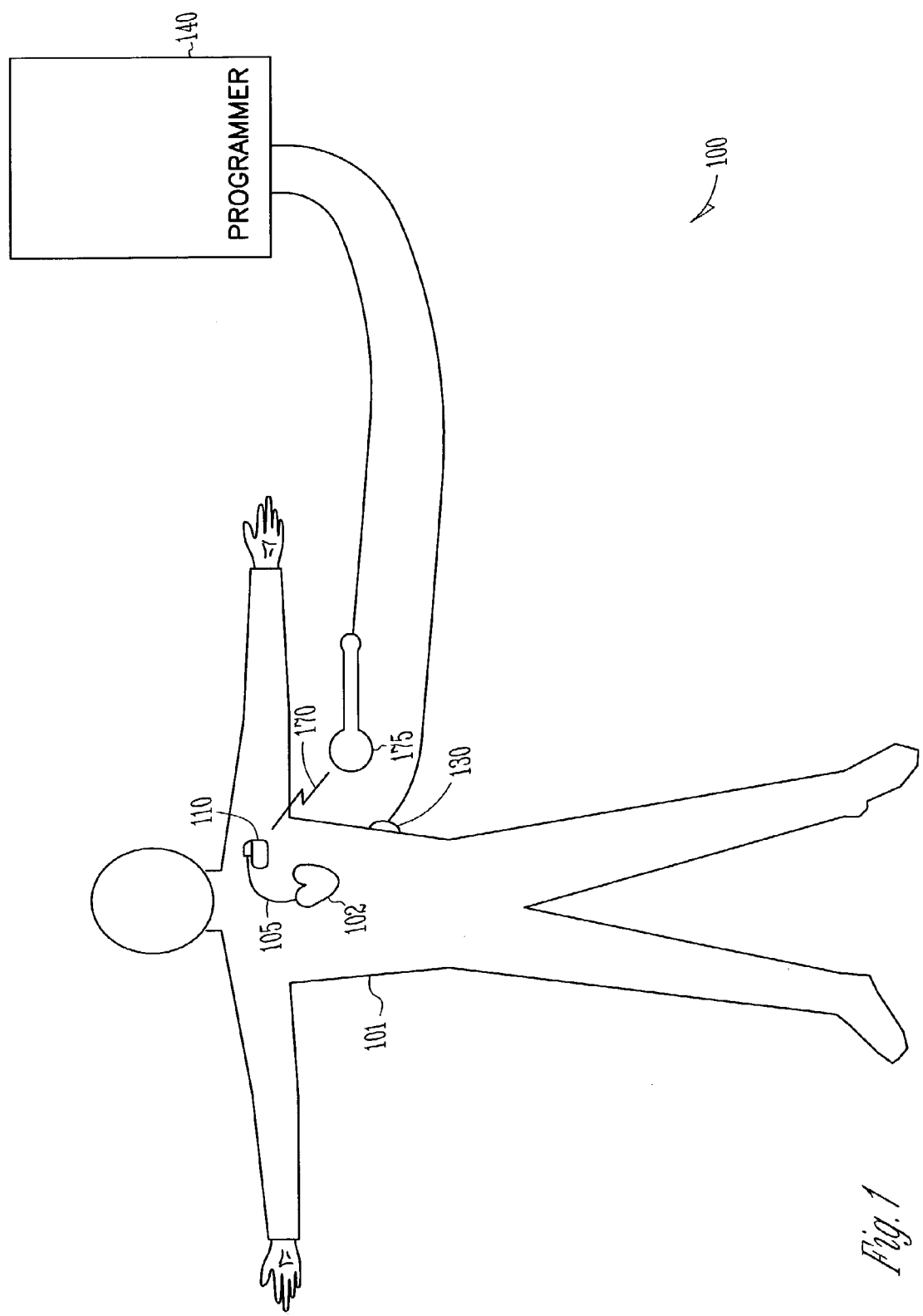
FIG. 1 is a schematic illustration of an embodiment of portions of a cardiac rhythm management system and portions of an environment in which it is used.

FIG. 1 is a schematic illustration of an embodiment of portions of a cardiac rhythm management system 100 and portions of an environment in which it is used. In one embodiment, system 100 is a cardiac rhythm management system including, among other things, an implanted device 110 and an external programmer 140. Implanted device 110 is implanted within a patient's body 101 and coupled to the patient's heart 102 by a lead system 105. Examples of implanted device 110 include pacemakers, cardioverter/defibrillators, pacemaker/defibrillators, CRT devices, and drug delivery devices. Programmer 140 includes a user interface for system 100. Throughout this document, the "user" refers to a physician or other caregiver who examines and/or treats the patient with system 100. The user interface allows a user to interact with implanted device 110 through a telemetry link 170.

In one embodiment, as illustrated in FIG. 1, telemetry link 170 is an inductive telemetry link supported by a mutual inductance between two closely-placed coils, one housed in a wand 175 near or attached onto body 101 and the other housed in implanted device 110. In an alternative embodiment, telemetry link 170 is a far-field telemetry link. In one embodiment, telemetry link 170 provides for data transmission from implanted device 110 to programmer 140. This may include, for example, transmitting real-time physiological data acquired by implanted device 110, extracting physiological data acquired by and stored in implanted device 110, extracting therapy history data stored in implanted device 110, and extracting data indicating an operational status of implanted device 110 (e.g., battery status and lead impedance). In a further embodiment, telemetry link 170 provides for data transmission from programmer 140 to implanted device 110. This may include, for example, programming implanted device 110 to acquire physiological data, programming implanted device 110 to perform at least one self-diagnostic test (such as for a device operational status), and programming implanted device 110 to deliver at least one therapy.

In one embodiment, programming implanted device 110 includes sending therapy parameters to implantable device 110. In one embodiment, the therapy parameters provide an approximately optimal hemodynamic performance to a patient by delivering cardiac pacing pulses to the patient's heart. To determine approximately optimal therapy parameters, i.e., therapy parameters providing for the approximately optimal hemodynamic performance, there is a need to diagnose the heart's conditions and/or evaluate the hemodynamic performance with different therapy types and/or parameters. The need is met by using a phonocardiographic image simultaneously showing electrical events, mechanical events and electromechanical time intervals for multiple cardiac cycles. The electrical events include, by way of example, but not by way of limitation, intrinsic depolarizations and deliveries of pacing pulses. The mechanical events and electromechanical time intervals include, by way of example, but not by way of limitation, mitral valve closure, aortic valve opening and closure, electromechanical activation delays, isovolumic contraction time, ejection period, and diastolic filling period.

In one embodiment, the phonocardiographic image is formed based on a signal acquired by using an acoustic sensor placed in or about heart 102 to directly or indirectly sense heart sounds indicative of mechanical activities of heart 102. In one embodiment, the acoustic sensor is a microphone. In another embodiment, the acoustic sensor is an accelerometer. In one embodiment, as shown in FIG. 1, the acoustic sensor is an external sensor 130 attached on to body 101 near heart 102. External sensor 130 is connected to programmer 140 via a cable through which an acoustic sensor signal representing heart sounds is transmitted to programmer 140. In another embodiment, the acoustic sensor is an implanted acoustic sensor that is housed in implanted device 110 or otherwise connected to implanted device 110. An acoustic sensor signal representing heart sounds is transmitted to programmer 140 via telemetry link 175.

Figure 2:
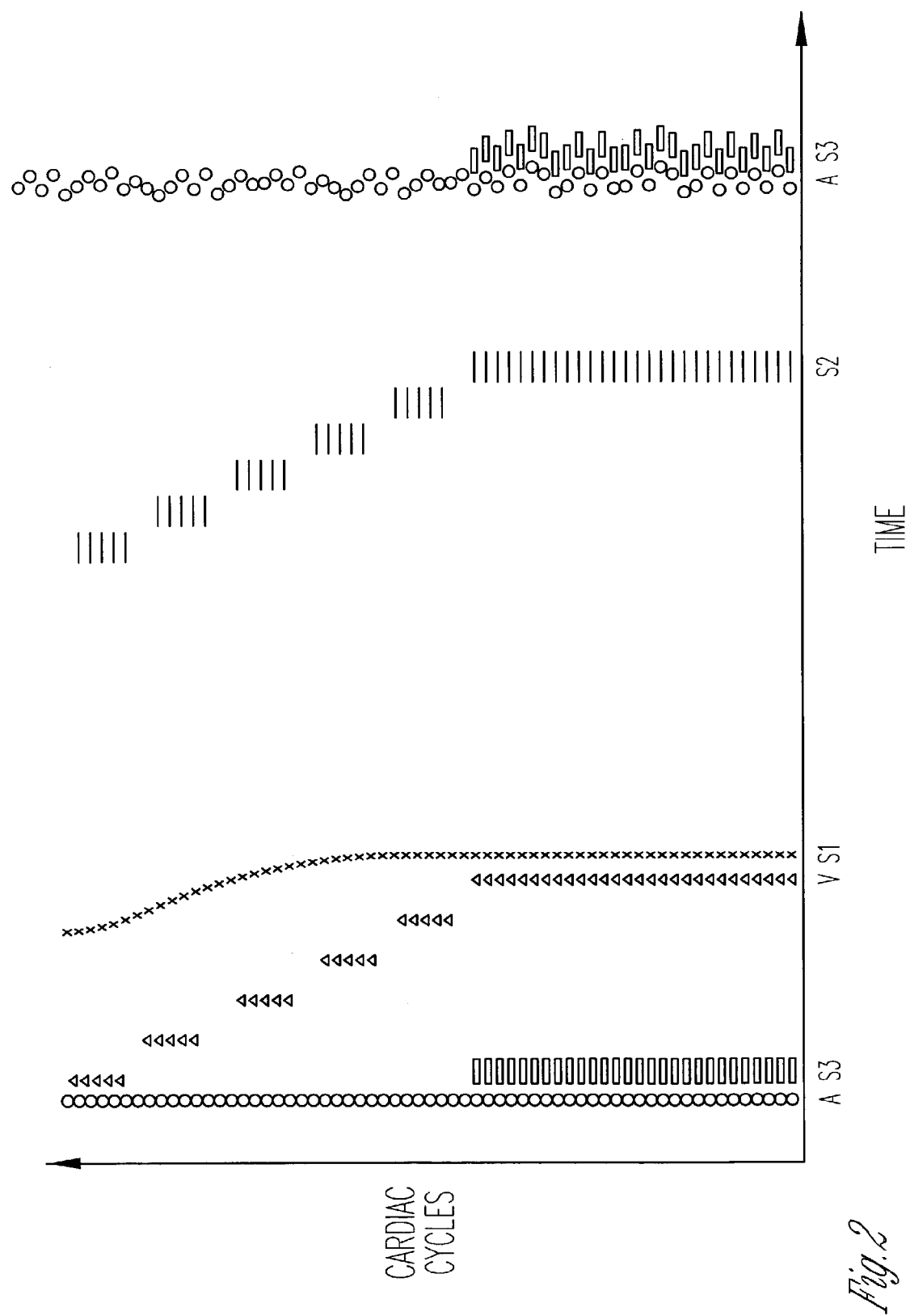
FIG. 2 is a conceptual illustration of one embodiment of a phonocardiographic image constructed of an acoustic sensor signal.

FIG. 2 is a conceptual illustration of one embodiment of the phonocardiographic image. The phonocardiographic image simultaneously presents multiple cardiac cycles each including representations or indications of electrical and mechanical events of heart 102 that occur during the cycle. In one embodiment, the electrical events include intrinsic depolarizations sensed from, and pacing pulses delivered to, heart 102. These electrical events are referred to as cardiac events. In one embodiment, the mechanical events of heart 102 are indicated by heart sounds. In one embodiment, as illustrated in FIG. 2, the phonocardiographic image includes a horizontal axis indicating time and a vertical axis indicating cardiac cycles. The cardiac events and heart sounds during each cardiac cycle is presented at the same vertical level. In one embodiment, the phonocardiographic image includes a stack of signal segments each represent at least one cardiac cycle including cardiac events and heart sounds detected during that cardiac cycle. In another embodiment, the phonocardiographic image includes stacked signal segments each represent at least a portion of a cardiac cycle including selected cardiac events and heart sounds detected during that cardiac cycle. In one embodiment, as illustrated in FIG. 2 by way of example, but not by way of limitation, the phonocardiographic image includes a stack of signal segments each include one complete cardiac cycle between two cardiac events A, and includes representations or indications of detected cardiac events A and V and heart sounds S1, S2, and S3. Cardiac event A represents an atrial event that is either an intrinsic depolarization sensed from an atrium or a pacing pulse delivery to the atrium. Cardiac event V represents a ventricular event that is either an intrinsic depolarization sensed from a ventricle or a pacing pulse delivery to the ventricle. Heart sound S1 represents the "first heart sound," which is known to be indicative of, among other things, mitral valve closure, tricuspid valve closure, and aortic valve opening. Heart sound S2 represents the "second heart sound," which is known to be indicative of, among other things, aortic valve closure and pulmonary valve closure. Heart sound S3 represents the "third heart sound," which is known to be indicative of certain pathological conditions including heart failure. In other embodiments, the phonocardiographic image include representations and/or indications of one or more of other cardiac events and heart sounds such as the "fourth heart sound" and various components of the first, second, and third heart sounds.

In one embodiment, the phonocardiographic image includes the stack of signal segments aligned by a selected cardiac event or heart sound that presents during each cardiac cycle. This facilitates observation of trends of times of heart sounds and/or time intervals between any two of the cardiac events and heart sounds over multiple cardiac cycles. In one embodiment, as illustrated in FIG. 2, the signal segments are aligned by cardiac event A. This allows, for example, observation of a trend of the A-S1 interval, indicative of an electromechanical interval between atrial contraction and mitral valve closure (A-MC interval), over multiple cardiac cycles. In another embodiment, the signal segments are aligned by cardiac event V. Generally, any repetitious cardiac event or heart sound can be used for the alignment of the signal segments, depending on the specific need to facilitate observation of, or detection from, the phonocardiograph image. In one embodiment, as illustrated in FIG. 2, the A-S1 interval trend indicates the effect of a shortened A-V time interval on the timing of mitral valve closure. In one embodiment, the shortened A-V time interval is a result of cardiac pacing using an atrio-ventricular delay (AVD) that is shorter than an intrinsic atrio-ventricular interval (AVI). In other embodiments, the signal segments may be aligned by any of the cardiac events and heart sounds represented or indicated in the phonocardiograph image, such as any of A, V, S1, S2, and S3, for example, depending on the specific trend to be observed.

In one embodiment, the phonocardiographic image includes the stack of signal segments arranged in a selected order. This further facilitates the observation of the timing trends. In one embodiment, the signal segments are arranged by the values of a specific timing interval or parameter associated with each of the signal segments to facilitate observation of the timing trends over the specific timing interval or parameter. In one embodiment, as illustrated in FIG. 2, the signal segments are arranged by the values of the A-V time interval. This facilitates observation of the A-S1 interval trend over the A-V time interval. When the A-V time interval varies as a result of cardiac pacing at various AVDs, the phonocardiographic image facilitates observation of the trend of the A-S1 interval over AVDs of the cardiac pacing. In a further embodiment, selected signal segments such as the signal segments associated with the same A-V time interval are averaged. When the A-V time interval varies as a result of cardiac pacing at various AVDs, the phonocardiographic image facilitates observation of the trend of the averaged A-S1 interval over AVDs of the cardiac pacing. In another further embodiment, one of the AVDs is selected based on a desirable A-S1 interval indicative of an approximately optimal electromechanical interval between atrial contraction and mitral valve closure. In another related embodiment, as illustrated in FIG. 2, heart sound S3 is observed to be present only during the cardiac cycles or signal segments associated with relatively long A-V time intervals. This indicates that pacing improves cardiac conditions of a heart failure patient by shortening the A-V time interval. In other embodiments, the signal segments may be arranged by any of the intrinsic and therapy time intervals observable from the phonocardiographic image, depending on the trend to be observed. For example, if the trend of an electromechanical interval over heart rate and/or pacing rate is of interest, the signal segments may be arranged by the atrial cycle length interval (time interval between two consecutive cardiac events A) or the ventricular cycle length interval (time interval between two consecutive cardiac events V).

Figure 3:
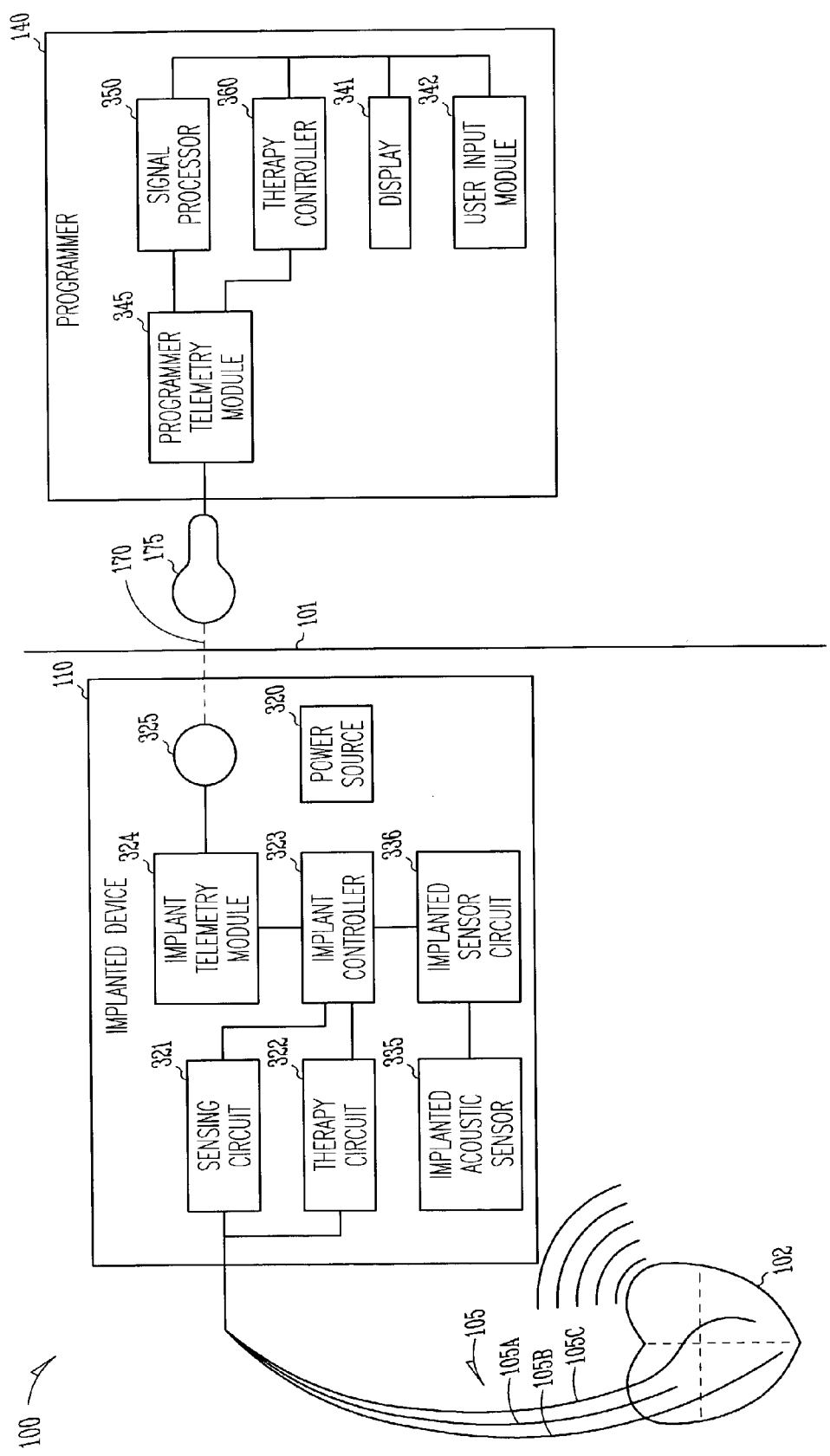
FIG. 3 is a schematic/block diagram illustrating one embodiment of portions of the cardiac rhythm management system with an implanted acoustic sensor.

FIG. 3 is a schematic/block diagram illustrating one embodiment of portions of cardiac rhythm management system 100 with an implanted acoustic sensor 335. System 100 provides for acquisition of at least a cardiac signal and an acoustic sensor signal indicating the cardiac events and heart sounds represented or indicated in the phonocardiographic image. In one embodiment, system 100 includes an implanted portion and an external portion. The implanted portion resides within body 101 and includes implanted device 110 and lead system 105 providing for electrical connection between implanted device 110 and heart 102. The external portion includes programmer 140 and wand 175 connected to programmer 140. Telemetry link 170 provides for bi-directional communications between implanted device 110 and programmer 140.

In one embodiment, lead system 105 includes one or more leads having endocardial electrodes for sensing cardiac signals referred to as intracardiac ECGs, or electrograms. In one embodiment, lead system 105 includes at least an atrial lead and a ventricular lead. In one embodiment, as illustrated in FIG. 3, lead system 105 includes an atrial lead 105A having at least one electrode placed within the right atrium, a right ventricular lead 105B having at least one electrode placed within the right ventricle, and a left ventricular lead 105C having at least one electrode placed in or about the left ventricle. In one specific embodiment, lead 105C includes at least one electrode placed in coronary venous vasculature traversing the left ventricle. Such lead system allows for CRT including left ventricular, right ventricular, or biventricular pacing.

In one embodiment, implanted device 110 includes a sensing circuit 321, a therapy circuit 322, an implant controller 323, an implant telemetry module 324, a coil 325, an implanted acoustic sensor 335, an implanted sensor circuit 336, and a power source 320. Sensing circuit 321 includes one or more sensing amplifiers each sense a cardiac signal from a cardiac location where an endocardial electrode of lead system 105 is placed. Therapy circuit 322 includes one or more therapy output circuits that deliver one or more therapies to heart 102. In one embodiment, therapy circuit 322 includes one or more pacing output circuits each deliver pacing pulses to a cardiac location where an endocardial electrode of lead system 105 is placed. In another embodiment, therapy circuit 322 includes one or more defibrillation output circuits each deliver defibrillation shocks to a cardiac location. In a further embodiment, therapy circuit 322 includes one or more pacing output circuit and one or more defibrillation output circuits. Implanted acoustic sensor 335 senses an acoustic signal including heart sounds indicative of mechanical events of heart 102 and converts the acoustic signal to an acoustic sensor signal representing the acoustic signal. In one embodiment, the acoustic sensor signal has a voltage amplitude associated with the intensity of the acoustic signal. In one embodiment, implanted acoustic sensor 335 includes a microphone. In another embodiment, implanted acoustic sensor 335 includes an accelerometer. In one embodiment, the accelerometer is also used to sense movements of implanted device 110 or body 101 to monitor a metabolic need of the organs of body 101. Implant controller 323 controls the operation of implanted device 110. In one embodiment, implant controller 323 includes a memory circuit on which therapy instructions and parameters are stored. The controller executes the therapy instructions to deliver one or more therapies to heart 102 with the therapy parameters. In one embodiment, the therapy instructions are programmed into the memory circuit when implant device 110 is built, and the therapy parameters are programmed into the memory circuit by programmer 140 via telemetry link 170. In another embodiment, both the therapy instructions and parameters are programmed to the memory circuit by programmer 140 via telemetry link 170. In one embodiment, the therapy parameters stored in the memory circuit are dynamically updated by programmer 140 via telemetry link 170 during or between therapy deliveries. In one embodiment, the therapy instructions includes a therapy algorithm that controls each therapy delivery based on one or more cardiac signals sensed through lead system 105 and sensing circuit 321, the acoustic sensor signal acquired through implanted acoustic sensor 335 and implanted sensor circuit 336, and the therapy parameters. In one embodiment, the therapy includes a pacing therapy; the therapy instructions includes at least one pacing algorithm that controls delivery of pacing pulses on a beat-by-beat basis based on the one or more cardiac signals, the acoustic sensor signal, and pacing parameters stored in the memory circuit. In one specific embodiment, the therapy instructions stored in the memory circuit include therapy instructions for pacing modes of at least a VDD type and a DDD type. The therapy parameters stored in the memory circuit include pacing parameters including at least one AVD. In this embodiment, implant controller 323 times each delivery of a pacing pulse to the heart. In one embodiment, implant controller 323 processes the one or more cardiac signals and acoustic sensor signals to control the therapy deliveries and to transmit the signals or their representations to programmer 140 through telemetry link 170. In one embodiment, implant controller 323 detects cardiac events from the cardiac signals and marks each detected cardiac events with event markers each indicative of a type and an approximate time of occurrence or detection of a detected cardiac event. In this embodiment, therapy deliveries are also marked with other event markers each indicative of a type and an approximate time of delivery of a therapy. In one specific embodiment, each delivery of the therapy is a delivery of a pacing pulse. In one embodiment, event markers representing detected cardiac events and therapy deliveries are transmitted to programmer 140 via telemetry link 170. Implant telemetry module 324 and coil 325 constitute portions of implanted device 110 that support telemetry link 170.

In one embodiment, controller 323 controls the transmission of signals acquired by implanted device 110 to programmer 140 via telemetry link 170. The signals include the cardiac signal and/or the acoustic sensor signal. In one embodiment, controller 323 digitizes the signals such that cardiac signal samples and/or acoustic sensor signal samples are transmitted to programmer 140 via telemetry link 170.

In one embodiment, all the components of implanted device 110, including sensing circuit 321, therapy circuit 322, implant controller 323, implant telemetry module 324, coil 325, implanted acoustic sensor 335, implanted sensor circuit 336, and a power source 320, are housed in a hermetically sealed metal can. In another embodiment, implanted acoustic sensor 335 is external to the can but is electrically connected to implanted sensor circuit 336 housed within the can. In a further embodiment, implanted acoustic sensor 335 is attached to a lead of lead system 105 and placed in heart 102. It is electrically connected to implanted sensor circuit 336 housed within the can through the lead. In one specific embodiment, the lead has a proximal end connected to sensing circuit 321 and a distal end disposed in the heart. Implanted acoustic sensor 335 is attached to the lead at or near its distal end.

Power source 320 supplies all energy needs of implanted device 110. In one embodiment, power source 320 includes a battery or a battery pack. In a further embodiment, power source 320 includes a power management circuit to minimize energy use by implant device 110 to maximize its life expectancy.

In one embodiment, programmer 140 includes a signal processor 350, a therapy controller 360, a display 341, a user input module 342, and a programmer telemetry module 345. Programmer telemetry module 345 and wand 175, which is electrically connected to programmer telemetry module 345, constitute portions of programmer 140 that support telemetry link 170. In one embodiment, signal processor 350 receives signals transmitted from implanted device 110 via telemetry link 170 and processes the signals for presentation on display 341 and/or use by therapy controller 360. The received signals may include the one or more cardiac signals, representations of cardiac events such as the event markers, and the acoustic sensor signal. In one embodiment, signal processor 350 includes an image formation module that forms a phonocardiographic image based on the concepts discussed above with reference to FIG. 2. Details about the image formation module are discussed below, with reference to FIG. 5. In one embodiment, therapy controller 360 generates therapy parameters to be transmitted to implanted device 110 via telemetry link 170. In one embodiment, therapy controller 360 receives user-programmable parameters from user input module 342 and converts them into code recognizable by implanted device 110. In another embodiment, therapy controller 360 includes an automatic therapy protocol execution module that generates therapy parameters based on a therapy protocol defining a sequences of therapies each being applied for a certain time period or number of heart beats. This allows for identifying a therapy producing desirable result such as the approximately optimal hemodynamic performance. Details about the therapy protocol and the automatic therapy protocol execution module are discussed below with reference to FIG. 6. Signals acquired by implanted device 110 and processed by signal processor 350, including the phonocardiographic image, are presented on display 341. In one embodiment, where the acoustic sensor signal is digitized, signal processor 350 converts acoustic sensor signal samples to image pixels for presentation on display 341. In one embodiment, user input module 342 receives commands from the user to control or adjust the format of the presentation of the phonocardiographic image. In one embodiment, display 341 is an interactive display that includes at least portions of user input module 342, such that the user may enter commands by contacting display 341. In one embodiment, user input module 342 includes a zooming module to allow the user to enlarge a selected portion of the phonocardiographic image. In one embodiment, user input module 342 includes an electronic caliper module to allow the user to measure a time interval between any two points along any of the acoustic sensor signal segments. In one embodiment, user input module 342 comprises a video control module to allow the user to adjust at least one of a brightness, contrast, and color related to presenting the phonocardiographic image.

In one embodiment, programmer 140 is a computer-based device. In one specific embodiment, programmer 140 is built on a notebook computer. Signal processor 350 and therapy controller 360 are each implemented as one of a hardware, a firmware, a software, or a combination of any of these. In one embodiment, signal processor 350 and therapy controller 360 each include software that need to be installed on programmer 140 only if a phonocardiographic image based diagnosis or a phonocardiographic image based therapy parameter evaluation is intended to be performed with that programmer. In one embodiment, programmer 140 performs a variety of functions, including the phonocardiographic image-related functions as optional functions. The software supporting the phonocardiographic image-related functions are stored on one or more storage media for installation when needed.

Figure 4:
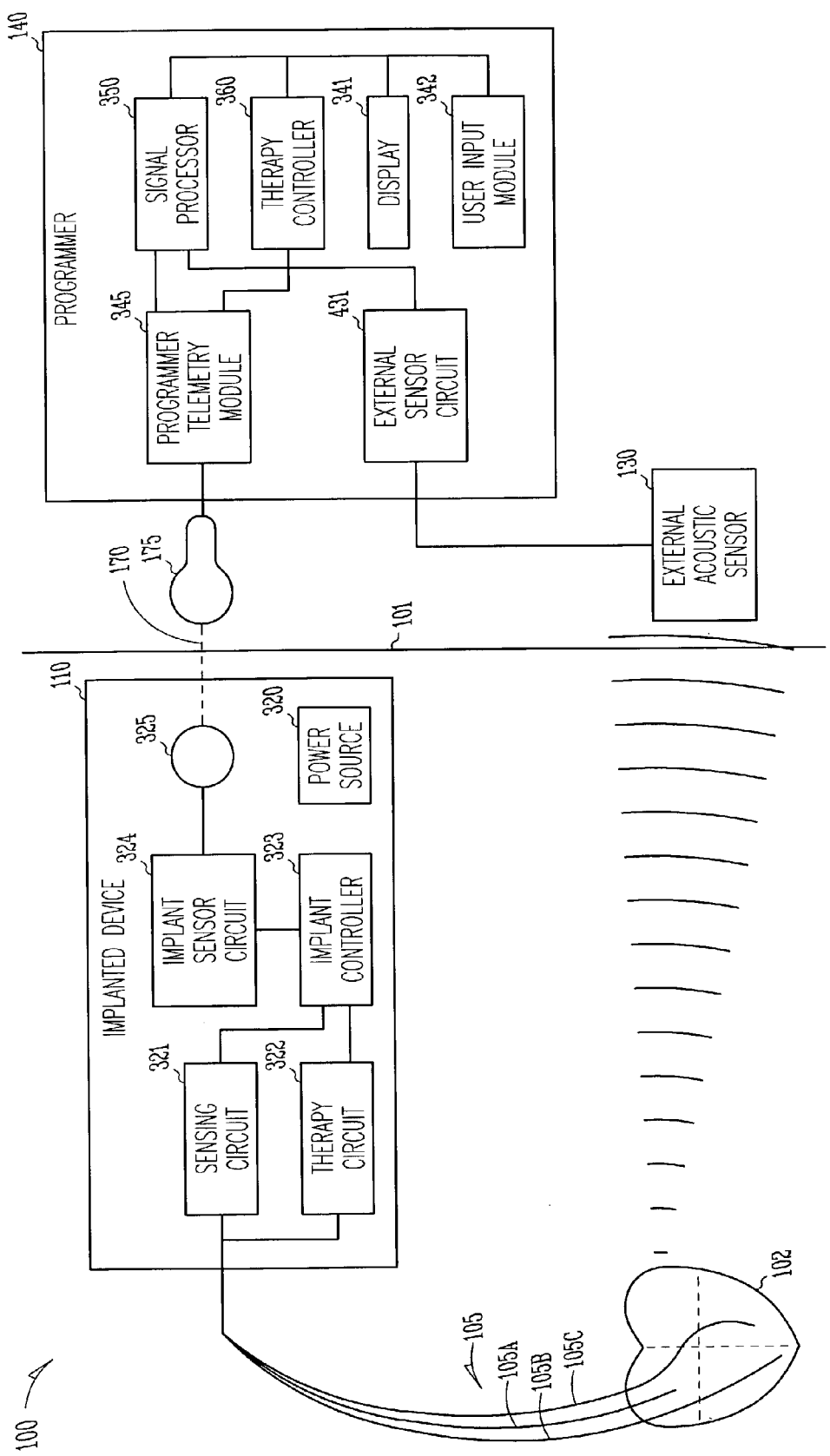
FIG. 4 is a schematic/block diagram illustrating one embodiment of portions of the cardiac rhythm management system with an external acoustic sensor.

FIG. 4 is a schematic/block diagram illustrating one embodiment of portions of the cardiac rhythm management system 100 with an external acoustic sensor. System 100 in this embodiment differs from system 100 in the embodiment of FIG. 3 in that the acoustic sensor is externally placed onto body 101. In this embodiment, system 100 includes external acoustic sensor 130 that is attached onto body 101. The location on body 101 where external acoustic sensor 130 is placed onto depends on the mechanical events of interest. For example, when external acoustic sensor 130 is used to detect the first heart sound indicative of mitral valve closure, the sensor is attached onto body 101 over heart 102 near its mitral valve. External acoustic sensor 130 is connected to an external sensor circuit 431, which processes the acoustic sensor signal for being received by signal processor 350. In one embodiment, external sensor circuit 431 digitizes the acoustic sensor signal to produce the acoustic sensor signal samples that are converted to image pixels for presentation on display 341. In another embodiment, signal processor 350 digitizes the acoustic sensor signal. In one embodiment, as illustrated in FIG. 4, external sensor circuit 431 is part of programmer 140. In an alternative embodiment, external sensor circuit 431 is connected to programmer 140 and functions as an interface between external acoustic sensor 130 and programmer 140.

In addition to the embodiments discussed with reference to FIG. 3 and FIG. 4, the phonocardiographic image can be formed with a cardiac signal and an acoustic sensor signal acquired by any implanted or external system providing for ECG and heart sound monitoring. In one embodiment, a surface electrode system including two or more surface ECG electrodes are attached to the skin of the patient to sense a surface ECG as the cardiac signal used to form the phonocardiographic image.

Figure 5:
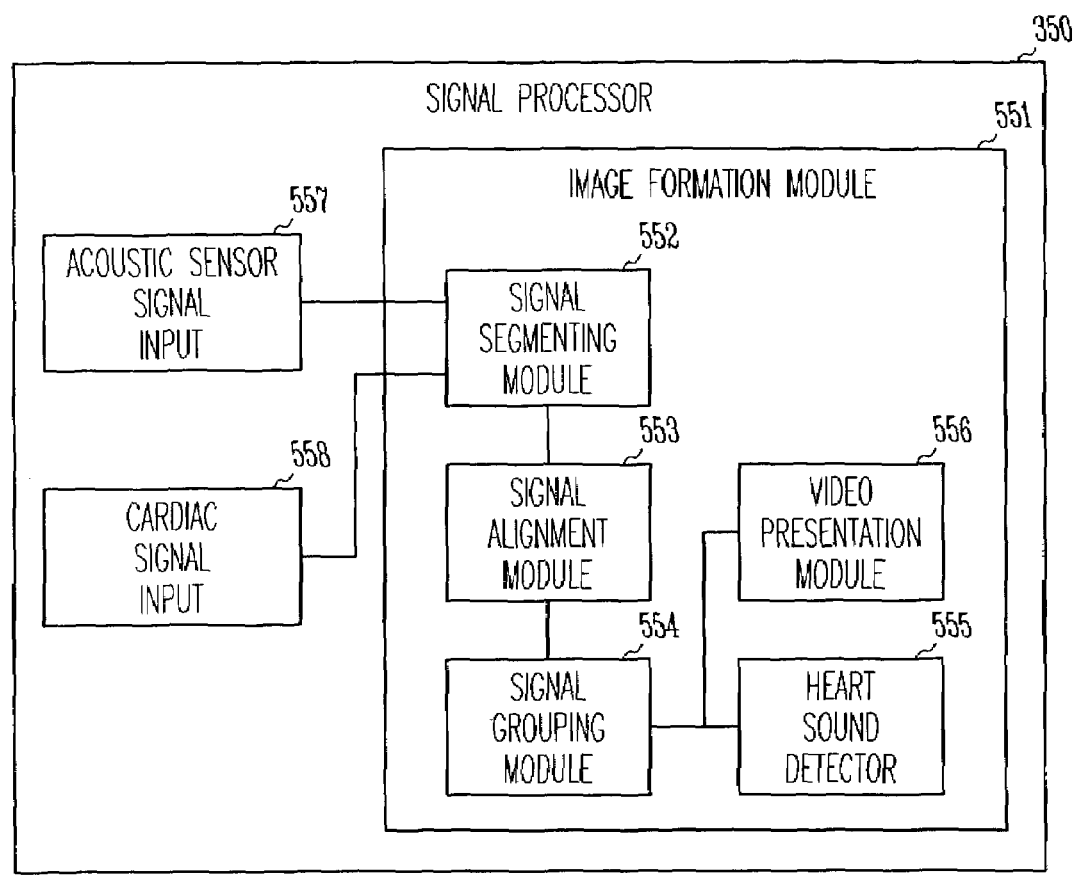
FIG. 5 is a schematic/block diagram illustrating one embodiment of a signal processor of the cardiac rhythm management system.

FIG. 5 is a schematic/block diagram illustrating one embodiment of signal processor 350. Among other functions, signal processor 350 produces the phonocardiographic image. In one embodiment, signal processor 350 includes, among other functional components, an acoustic sensor signal input 557, a cardiac signal input 558, and an image formation module 551. In one embodiment, acoustic sensor signal input 557 receives the acoustic sensor signal sensed by implanted acoustic sensor 335 and transmitted to programmer 140 via telemetry link 170. In an alternative embodiment, acoustic sensor signal input 557 receives the acoustic sensor signal sensed by external acoustic sensor 130 and transmitted to programmer 140 via wired electrical connections. In one embodiment, cardiac signal input 558 receives the one or more cardiac signals sensed by sensing circuit 321 and transmitted to programmer 140 via telemetry link 170. The cardiac signals each include indications of intrinsic depolarizations and therapy deliveries. In another embodiment, cardiac signal input 558 receives the event markers representative of the intrinsic depolarizations and therapy deliveries.

In one embodiment, image formation module 551 includes a signal segmenting module 552, a signal alignment module 553, a signal grouping module 554, a heart sound detector 555, and a video presentation module 556. In one embodiment, signal segmenting module 552 partitions the acoustic sensor signal into segments each including at least one complete cardiac cycle. In another embodiment, signal segmenting module 552 partitions the acoustic sensor signal into segments each including at least a portion of each cardiac cycle that includes all the required or desirable representations or indications of the cardiac events and heart sounds within that cardiac cycle. In a further embodiment, signal segmenting module 552 partitions the acoustic sensor signal based on a selected type of cardiac events or heart sounds. This facilitates observation of timing trends of cardiac events and heart sounds relative to the selected type of cardiac events. Signal alignment module 553 aligns all the acoustic sensor signal segments by the selected type of cardiac events or heart sounds. This facilitates observation of timing trends related to the heart sounds, especially time intervals between a selected type of the heart sounds and the selected type of cardiac events. Signal grouping module 554 sorts and groups the acoustic sensor signal segments according to a grouping instruction such that the phonocardiographic image presents the acoustic sensor signal segments in a predetermined order or arrangement. In one embodiment, signal grouping module 554 sorts and groups the acoustic sensor signal segments based on one or more of therapy parameters and cardiac parameters as provided by the grouping instruction, such as pacing rate, AVD, heart rate, and cardiac cycle length intervals (atrial cycle length interval and ventricular cycle length interval). This allows observation and analysis of heart sounds in relation with such one or more therapy parameters or cardiac parameters. In a further embodiment, signal grouping module 554 includes a signal segment averaging module that averages acoustic sensor signal segments selected according to the grouping instruction. In one specific embodiment, the signal segment averaging module averages the acoustic sensor signal segments associated with a common therapy or cardiac parameter value or range of values. In one embodiment, the grouping instruction, including the predetermined order or arrangement and/or the acoustic sensor signal segment averaging, is entered by the user through user input module 342. Heart sound detector 555 detects a selected type of heart sounds and presents representations of the detected heart sounds in the phonocardiographic image to further facilitate the observation of timing trends. In one embodiment, heart sound detector 555 detects a beginning, or a leading edge, of each of the selected type of heart sounds. In one embodiment, heart sound detector 555 detects heart sounds by using filtering techniques that are discussed in Carlson et al., U.S. Pat. No. 5,674,256, entitled "CARDIAC PRE-EJECTION PERIOD DETECTION," assigned to Cardiac Pacemakers, Inc., the disclosure of which is incorporated herein by reference in its entirety. In one embodiment, video presentation module 556 converts the acoustic sensor signal samples to image pixels for presentation on display 341. Information included in the acoustic sensor signal, such as intensity of heart sounds, is coded in the image pixels. In one embodiment, each image pixel represents a single acoustic sensor signal sample. In another embodiment, each image pixel represents a value calculated from a predetermined number of acoustic sensor signal samples using a predetermined mathematical formula. In one specific embodiment, video presentation module 556 averages several acoustic sensor signal samples to present an acoustic sensor signal segment indicative of heart sounds with an intensity averaged over a predetermined number of cardiac cycles. In one embodiment, video presentation module 556 includes an image enhancer. In one specific embodiment, video presentation module 556 filters the acoustic signal segments to enhance the phonocardiographic image by increasing the contrast.

In one embodiment, at least portions of signal processor 350, including acoustic sensor signal input 557, cardiac signal input 558, and image formation module 551, are implemented as software. In one embodiment, this software is a stand-alone software, or a portion thereof, that is stored on a compute-readable storage medium. In one embodiment, this software is installed in a computer for an off-line analysis based on recorded cardiac signal and acoustic sensor signal.

Figure 6:
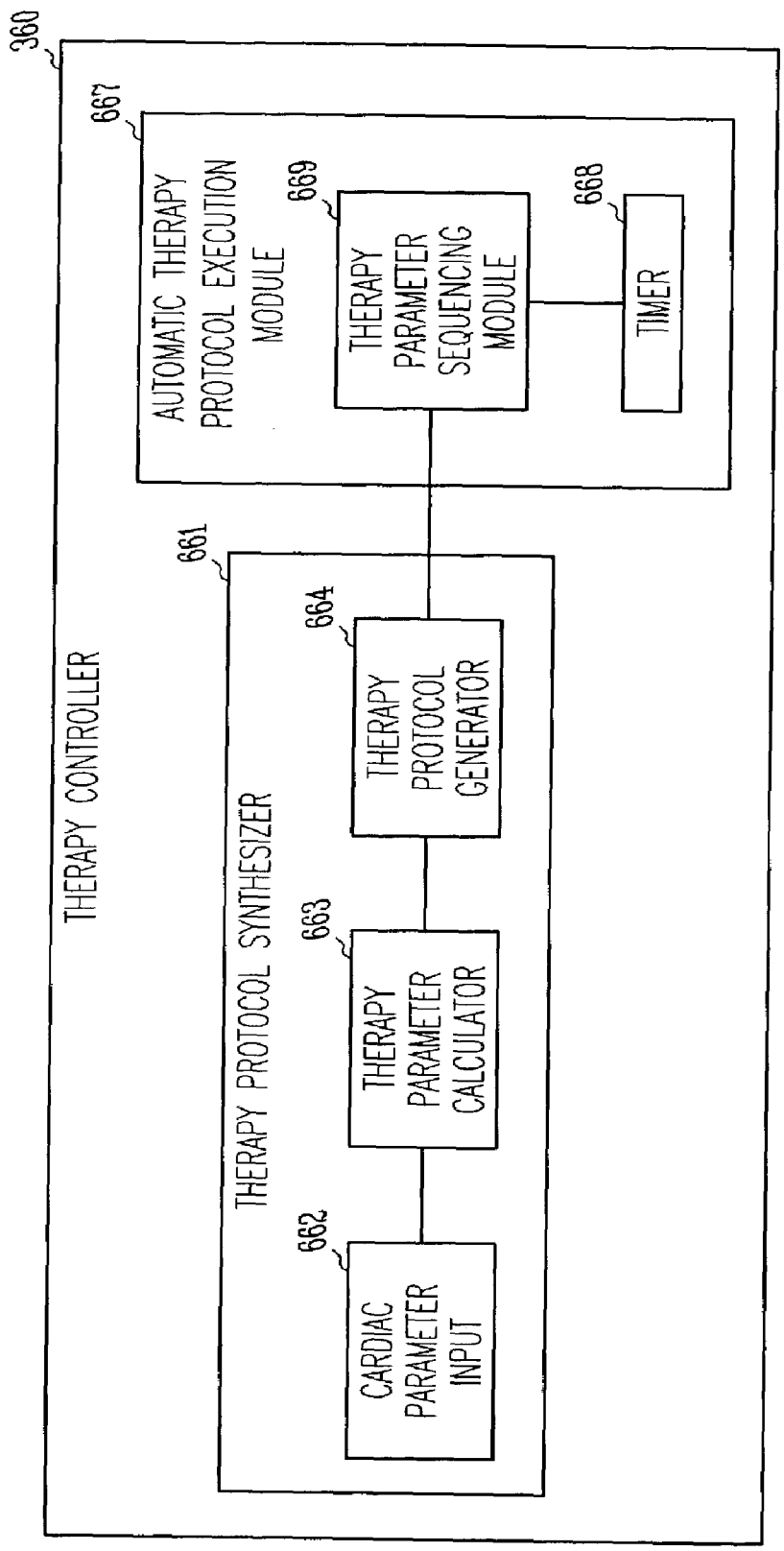
FIG. 6 is a schematic/block diagram illustrating one embodiment of a therapy controller of the cardiac rhythm management system.

FIG. 6 is a schematic/block diagram illustrating one embodiment of therapy controller 360. Therapy controller 360 allows the user to, for example, select a therapy, start the therapy, stop the therapy, and adjust parameters associated with the therapy. In one embodiment, therapy controller 360 converts user commands and selections received by user input module 342 to codes recognizable by implanted device 110, and sends the codes to implanted device 110 through telemetry link 170. In one embodiment, therapy controller 360 includes, among other functional components, a therapy protocol synthesizer 661 and an automatic therapy protocol execution module 667. In one embodiment, a therapy protocol includes therapy descriptions including a sequence of therapy parameter sets defining a sequence of therapies to be evaluated with a patient. In one embodiment, the therapy protocol defines a time period or a number of heart beats over which each of the therapies is to be delivered. In one embodiment, the therapy protocol includes therapy descriptions defining a sequence of therapies of the same type but each including at least one parameter whose value differs from that of the other therapies. In one embodiment, the therapy protocol includes therapy descriptions defining a sequence of alternating therapies and non-therapies. In other words, a "resting" or "washing" period is provided between therapy deliveries, such that the effects of each therapy can be isolated for analysis. The purpose for executing such a therapy protocol includes identifying a therapy type and/or a therapy parameter or parameter set associated with a desirable therapeutic result. In one embodiment, the therapeutic result is observed from the phonographic image discussed above with reference to FIG. 2.

In one embodiment, therapy protocol synthesizer 661 includes a cardiac parameter input 662, a therapy parameter calculator 663, and a therapy protocol generator 664. Cardiac parameter input 662 receives at least one cardiac parameter related to the patient. In one embodiment, the cardiac parameter is entered by the user. In another embodiment, the cardiac parameter is measured by signal processor 350 from the cardiac signals and/or event markers telemetered from implanted device 110. Therapy parameter calculator 663 calculates a series of therapy parameters based on the cardiac parameter. Therapy protocol generator 664 generates the therapy descriptions defining a sequence of therapies each including a parameter set defining a therapy using the calculated therapy parameters.

In one embodiment, automatic therapy protocol execution module 667 includes a therapy parameter sequencing module 669 and a timer 668. Therapy parameter sequencing module 669 sends the therapy descriptions defining a sequence of therapies to implanted device 110 via telemetry link 170, one portion (description of one of the sequence of therapies) at a time, as timed by timer 668. In one embodiment, therapy parameter sequencing module 669 sends a description containing a complete parameter set defining a therapy before or at the beginning of a protocol execution, and then sends further therapy descriptions containing only therapy parameters whose values change during the protocol execution. In one embodiment, timer 668 starts timing a predetermined time period when therapy parameter sequencing module 669 sends a therapy description. It signals therapy parameter sequencing module 669 to send the next therapy description after the time period has elapsed. In another embodiment, timer 668 includes a heart beat counter that starts beat counting when therapy parameter sequencing module 669 sends a therapy description. It signals therapy parameter sequencing module 669 to send the nest therapy description after a predetermined number if beats have been counted.

In one embodiment, the therapy protocol is a pacing protocol designed to evaluate pacing parameters by observing hemodynamic performance of the patient in response to pacing therapies using these pacing parameters. In one embodiment, the pacing protocol includes descriptions of a sequence of pacing patterns each including a distinctive AVD. The purpose for executing such a pacing protocol includes identification of an approximately optimal AVD, which is associated with the approximately optimal hemodynamic performance. In one embodiment, the pacing protocol includes AVDs calculated from a patient's intrinsic AVI or another measured physiological time interval. The pacing protocol includes a sequence of alternating pacing and non-pacing periods, with the calculated AVDs included in the pacing periods in a randomized order. In a further embodiment, the sequence is repeated for a number of times, with the order of the calculated AVDs randomized separately for each repetition. The purpose for alternating the pacing and non-pacing periods and repeating the sequence with individually randomized order of AVDs includes isolating the effect of pacing at each AVD during a statistical analysis of the results obtained by executing the pacing protocol with a patient.

Figure 7:
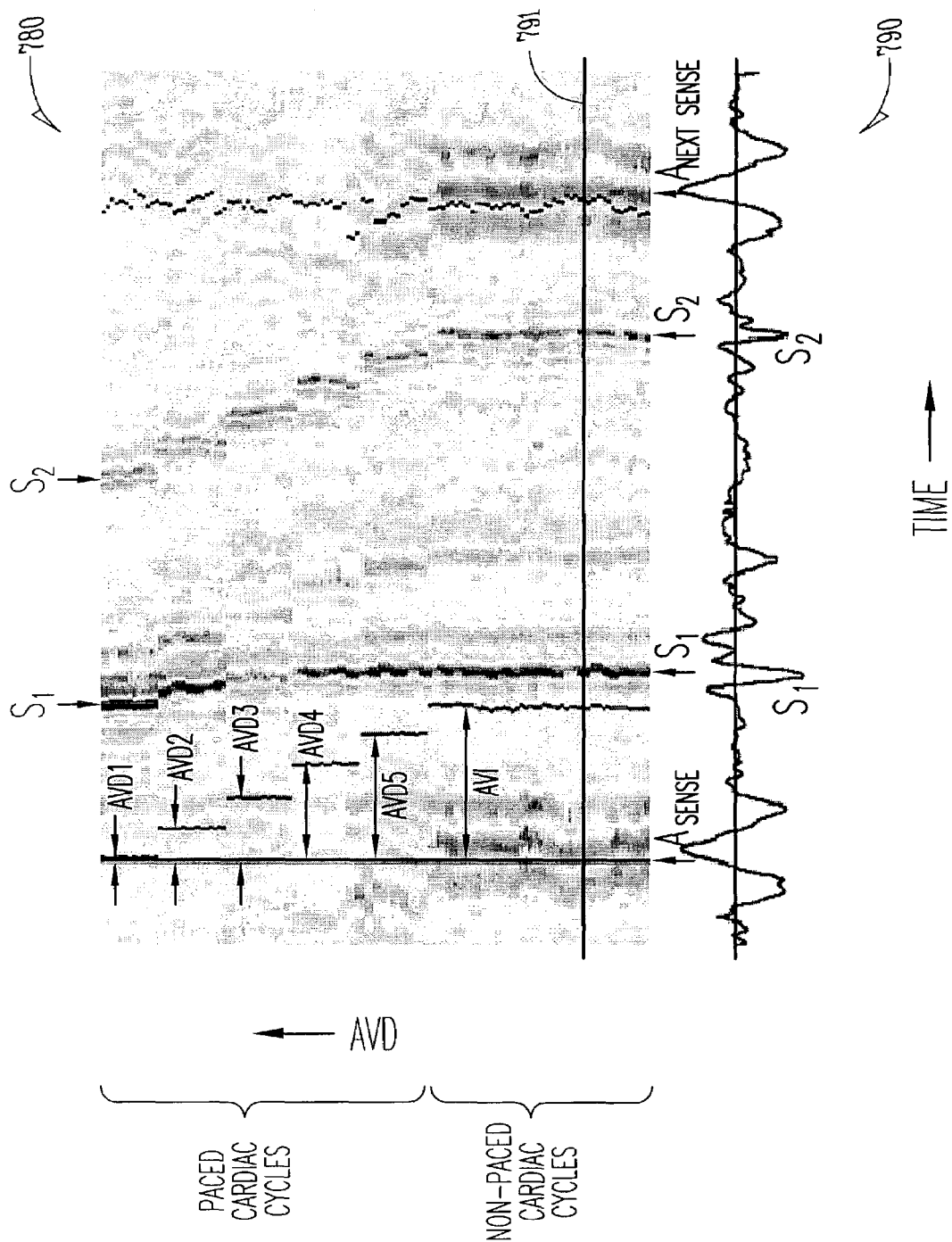
FIG. 7 is an illustration of portions of a visual presentation including an actual phonocardiographic image according to the embodiment of FIG. 2.

FIG. 7 is an illustration of portions of a visual presentation including an actual phonocardiographic image 780 according to the embodiment of FIG. 2. In one embodiment, the visual presentation is displayed on display 341. Phonocardiographic image 780 is shown in FIG. 7, by way of example, but not by way of limitation, an implementation of the concepts discussed above with reference to FIG. 2. It is formed based on cardiac events and an accelerometer signal recorded during a pacing protocol execution. The pacing protocol is designed to test the effect of atrial tracking mode pacing (VDD mode pacing with multiple ventricular sites) with five different AVDs, AVD1–AVD5, on the hemodynamic performance of a patient suffering congestive heart failure but having a normal sinus node. The pacing protocol includes a sequence of alternating pacing and non-pacing periods, with AVD1–AVD5 calculated based on an intrinsic AVI measured from the patient and included in the pacing periods in a randomized order. The sequence is repeated for a predetermined number of times for statistical significance of the results, with the order of AVD1–AVD5 randomized separately for each repetition.

In accordance with the concepts discussed above with reference to FIG. 2, phonocardiographic image 780 includes stacked accelerometer signal segments aligned by atrial sense markers (Asense) and arranged by the AVDs and AVI. Event markers temporally associated with each accelerometer signal segment are superimposed onto the accelerometer signal segment. Accelerometer signal segments associated with the AVI are resulted from the non-pacing periods, and accelerometer signal segments associated with the AVD1–AVD5 are resulted from periods of pacing at each of the AVDs. Ventricular event markers (V) present intrinsic ventricular depolarizations (when appearing on an accelerometer signal segment associated with the AVI) and deliveries of ventricular pacing pulses (when appearing on an accelerometer signal segment associated with one of the AVD1–AVD5).

In one embodiment, as illustrated in FIG. 7, amplitude of the acoustic sensor signal, indicative of presence and intensity of the heart sounds, is coded in the image pixels for presentation on display 341. In one specific embodiment, the amplitude of the acoustic sensor signal is coded in the image pixels such that the amplitude is indicated on display 341 by gray scales. Phonocardiographic image 780 shows the first heart sound S1, the second heart sound S2, and the third heart sound S3 as relatively darker portions of each accelerometer signal segment. In a further embodiment, the amplitude levels correspond to gray scales with user-adjustable mapping. User input module 342 includes a mapping module to map an intensity of the acoustic sensor signal to the gray scales according to user commands. In another embodiment, the amplitude of the acoustic sensor signal is coded in the pixels such that the amplitude is indicated in display 341 by colors. In a further embodiment, the amplitude levels correspond to a spectrum of colors with user-adjustable mapping. User input module 342 includes a mapping module to map an intensity of the acoustic sensor signal to the spectrum of colors according to user commands.

In one embodiment, display 341 is an interactive display coupled to user input module 342 such that the user may enter commands or select options through display 341. In one embodiment, the user may select one of the acoustic sensor signal segments (e.g., acoustic sensor signal segment 791) by pointing a cursor to it, and causes display 341 to further display a planar acoustic sensor signal-verses-time curve that is the presentation of the selected acoustic sensor signal segment presented in a different form (e.g., acoustic sensor signal-verses-time curve 790).

Figure 8:
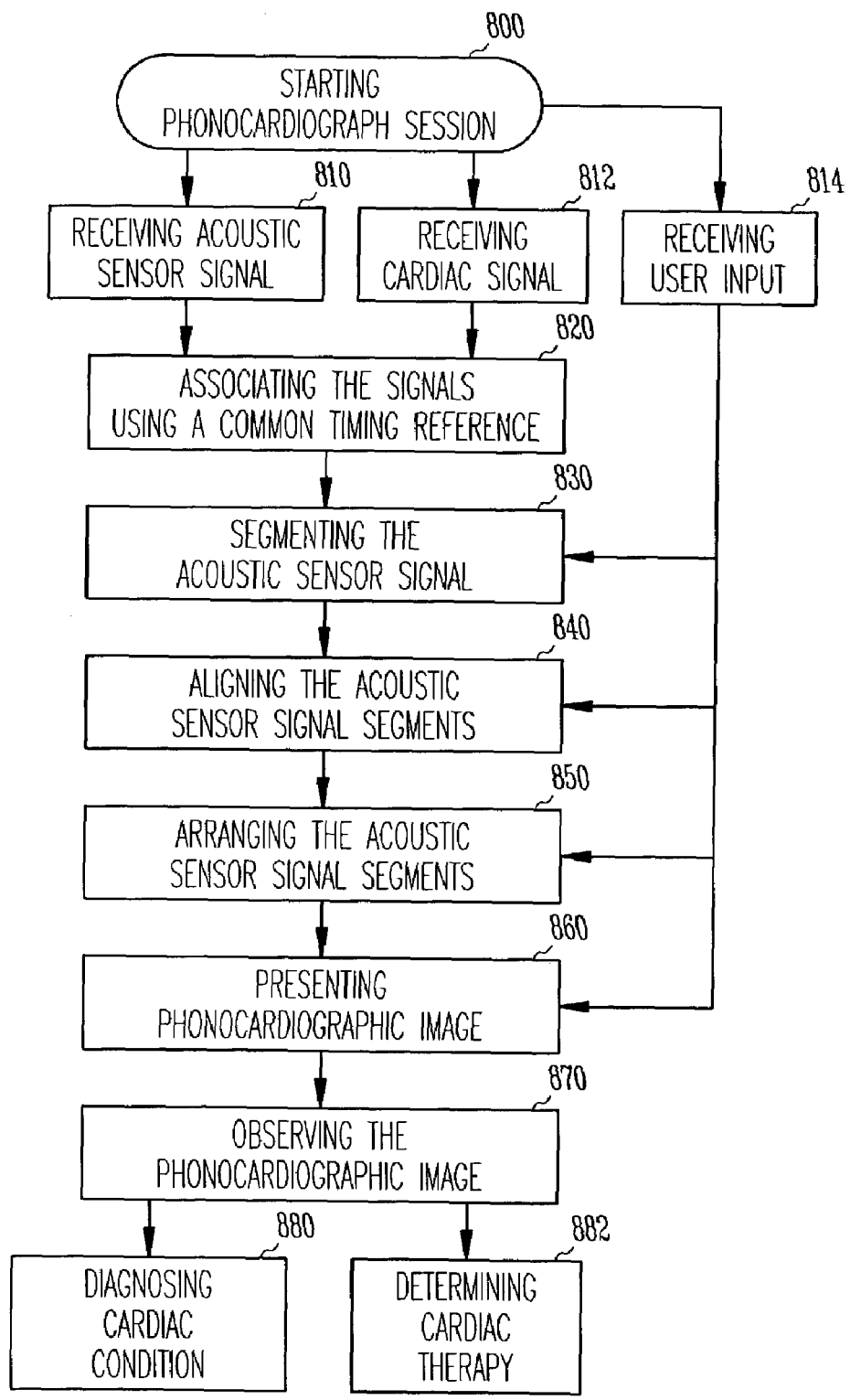
FIG. 8 is a flow chart illustrating one embodiment of a method for acquiring, presenting, and using the phonocardiographic image.

FIG. 8 is a flow chart illustrating one embodiment of a method for acquiring, presenting, and using the phonocardiographic image. At 800, a phonocardiograph session is started. In one embodiment, the user starts the phonocardiograph session by entering a command to programmer 140 through user input module 342. At 810, acoustic sensor signal input 557 receives an acoustic sensor signal indicative of mechanical events of heart 102. In one embodiment, the acoustic sensor signal is an accelerometer signal indicative of heart sounds. In an alternative embodiment, the acoustic sensor signal is a microphone signal indicative of heart sounds. At 812, cardiac signal input 558 receives a cardiac signal. In one embodiment, the cardiac signal is an intracardiac electrogram indicative of intrinsic cardiac depolarizations and therapy deliveries. In an alternative embodiment, the cardiac signal is a surface ECG. In another alternative embodiment, the cardiac signal includes event markers representative of intrinsic cardiac depolarizations and therapy deliveries. At 814, user input module 342 receives user instruction defining a presentation of the phonocardiographic image. The user instruction includes one or more types of the cardiac events or heart sounds used for segmenting and aligning the acoustic sensor signal segments, arrangement of the acoustic sensor signal segments for presentation, and other presentation format instructions. At 820, signal processor 350 associates the acoustic sensor signal and the cardiac signal by aligning the two signals to a common timing reference. In one embodiment, the acoustic sensor signal and the cardiac signal are received simultaneously. That is, steps 810 and 812 are performed simultaneously. Signal processor 350 aligns the acoustic sensor signal and the cardiac signal by aligning points or portions of the two signals that are recorded at the same time. At 830, signal segmenting module 552 partitions the received acoustic sensor signal into acoustic sensor signal segments. In one embodiment, the acoustic sensor signal segments each represent at least one cardiac cycle including representations or indications of the cardiac events and heart sounds detected during that cardiac cycle. In another embodiment, the acoustic sensor signal segments each represent at least a portion of a cardiac cycle including selected representations or indications of the cardiac events and heart sounds detected during that cardiac cycle. In one embodiment, points of segmenting are determined based on the user instruction received at 814. In this embodiment, signal segmenting module 552 partitions the acoustic sensor signal based on the one or more types of the cardiac events and heart sounds. In one embodiment, points of segmenting are related to times associated with the event markers. At 840, signal alignment module 553 aligns all the acoustic sensor signal segments by the selected type of cardiac events or heart sounds. In one embodiment, this alignment facilitates observation of timing trends related to the heart sounds, especially time intervals between a selected type of the heart sounds and the selected type of cardiac events. In one embodiment, the selected type of cardiac events includes atrial contraction. In another embodiment, the selected type of cardiac events includes ventricular contraction. In one embodiment, signal alignment module 553 aligns all the acoustic sensor signal segments by pre-selected type of cardiac events or heart sounds. In another embodiment, signal alignment module 553 aligns all the acoustic sensor signal segments according to the user instruction received at 814. At 850, signal grouping module 554 sorts and groups the acoustic sensor signal segments. In one embodiment, signal grouping module 554 sorts and groups the acoustic sensor signal segments to present them in a pre-defined or default order. In another embodiment, signal grouping module 554 sorts and groups the acoustic sensor signal segments to arrange them according to the user instruction received at 814. In one embodiment, signal grouping module 554 sorts and groups the acoustic sensor signal segments to present them in an order related to values of a therapy parameter or a measured cardiac parameter such as AVD, pacing rate, heart rate, and cardiac cycle length interval measured at an atrium or ventricle. In a further embodiment, signal grouping module 554 averages the acoustic sensor signal segments associated with one or more common values of the therapy parameter or the measured cardiac parameter such as AVD, pacing rate, heart rate, and cardiac cycle length interval measured at an atrium or ventricle. At 860, display 341 presents the phonocardiographic image including the aligned and grouped acoustic sensor signal segments. At 870, the user observes the phonocardiographic image. In one embodiment, the user observes from phonocardiographic image indications of at least one of events and time intervals such as mitral valve closure, aortic valve opening and closure, electromechanical activation delays, isovolumic contraction time, ejection period, and diastolic filling period.

In one embodiment, display 341 presents the phonocardiographic image and other information according to the user instruction received at 814. In one embodiment, display 341 displays a planar acoustic sensor signal-verses-time curve that is the presentation of a selected acoustic sensor signal segment presented in a different form. In one embodiment, display 341 enlarges a selected portion of the phonocardiographic image. In one embodiment, display 341 presents an electronic caliper movable by the user to measure a time interval between any two points along any of the acoustic sensor signal segments. In one embodiment, the user adjusts the brightness, contrast, and/or the color or gray scale mapping related to presenting the phonocardiographic image at 814. In one embodiment, receiving the user input at 814 including receiving portions of the user input along steps 810–870. In one embodiment, receiving the user input at 814, presenting the phonocardiographic image at 860, and observing the phonocardiographic image at 870 constitute an iterative process to result in a presentation that is satisfactory to the user.

Based on observing the phonocardiographic image at 870, the user may diagnose a cardiac condition at 880 and/or determine a cardiac therapy at 882. Details of steps 880 and 882 are discussed with reference to FIG. 9 and FIG. 10, respectively.

In one embodiment, the method illustrated in FIG. 8 is performed with programmer 140. In an alternative embodiment, the method illustrated in FIG. 8 is performed with a computer including components performing the functions of signal processor 350, display 341, and user input 342. In this alternative embodiment, the acoustic sensor signal and the cardiac signal are received at 810 and 812, respectively, from a storage medium on which the signals have been recorded with system 100.

Figure 9:
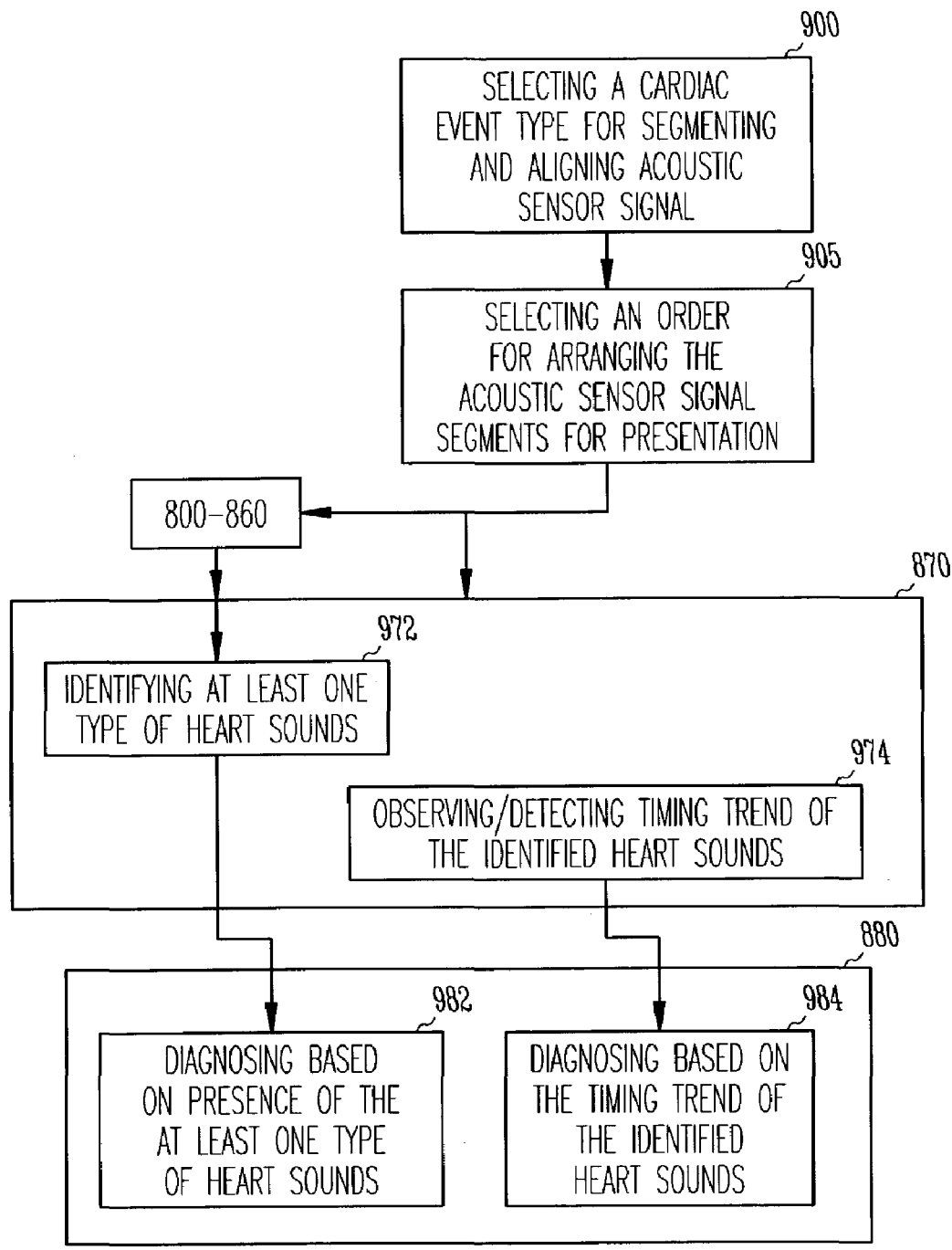
FIG. 9 is a flow chart illustrating one embodiment of a method for phonocardiographic image-based diagnosis.

FIG. 9 is a flow chart illustrating one embodiment of a method for phonocardiographic image-based diagnosis. One of the applications of the phonocardiographic image such as phonocardiographic image 780 is to provide a tool for diagnosis of cardiac conditions based on the acoustic sensor signal and the cardiac signal recorded from the patient, with or without delivering a cardiac therapy while recording the signals. In one embodiment, the phonocardiographic image-based diagnosis is performed on a patient suspected to have an abnormal cardiac condition. In another embodiment, the phonocardiographic image-based diagnosis is performed to a patient being a therapy candidate to determine whether a particular therapy is likely to improve the patient's cardiac conditions and hemodynamic performance. In yet another embodiment, the phonocardiographic image-based diagnosis is performed as a follow-up examination for a patient having been treated with a therapy. In one embodiment, the phonocardiographic image-based diagnosis provides a non-invasive way to examine a patient, with the cardiac signal and the acoustic sensor signal acquired through surface ECG electrodes and an external acoustic sensor. In another embodiment, the phonocardiographic image-based diagnosis provides a non-invasive way to examine a patient carrying an implanted device, with the cardiac signal and the acoustic sensor signal acquired by the implanted device and telemetered to an external device. In yet another embodiment, the phonocardiographic image-based diagnosis provides a non-invasive way to examine a patient carrying an implanted device, with the cardiac signal acquired by the implanted device and telemetered to an external device, and the acoustic sensor signal acquired by the external device through an acoustic sensor attached onto the patient.

The method for acquiring, presenting, and using the phonocardiographic image as discussed above with reference to FIG. 8 is incorporated into the method for the phonocardiographic image-based diagnosis. At 900, the user selects a type of cardiac events based on which the acoustic sensor signal is to be segmented and the acoustic sensor signal segments are to be aligned. In one embodiment, the user selects the type of cardiac events. In another embodiment, the user selects a type of diagnosis or a particular heart sound or a particular time interval to be observed, and signal processor 350 selects the cardiac event based on the user's selection. At 905, the user selects an order for arranging the acoustic sensor signal segments for presentation. In one embodiment, the user selects a timing interval and/or therapy parameter associated with each acoustic sensor signal segment. This timing interval and/or therapy parameter then determines the location of each acoustic sensor signal segment in the stack of the acoustic sensor signal segments of the phonocardiographic image. In another embodiment, the user selects a type of diagnosis or a particular heart sound or a particular time interval to be observed, and signal processor 350 sorts, groups, and arranges the acoustic sensor signal segments according to a predetermined default arrangement. In one embodiment, the selections made by the user at 900 and 905 are received by user input module 342 at 814.

For phonocardiographic image-based diagnostic purpose, observing the phonocardiographic image at 870 includes identifying at least one type of heart sounds at 972. This includes identifying a type such as the first, second, third, and fourth heart sound, or a component of one of these heart sounds. In one embodiment, observing the phonocardiographic image at 870 includes identifying one type of heart sounds based on the acoustic sensor signal amplitude and empirical knowledge temporal relation between the type of heart sounds and a type of cardiac events. In one embodiment, the user identifies the heart sound by observing the acoustic sensor signal amplitude represented by gray scales or colors. In a further embodiment, the user may adjust the amplitude-gray scale or amplitude-color mapping to change the contrast of the phonocardiographic image to facilitate the heart sound identification. In one embodiment, observing the phonocardiographic image at 870 further includes observing or detecting a timing trend of the identified type of heart sounds at 974. In one embodiment, the user observes the trend of an interval between a type of cardiac events and the identified type of heart sounds. In one specific embodiment, as illustrated in FIG. 7, the user observes the trend of the interval between atrial event Asense and heart sound S1 over the interval between Asense and V (i.e., AVD or AVI). This trend indicates the trend of the electromechanical interval between the atrial depolarization and the mitral valve closure over the atrio-ventricular activation interval. In another embodiment, heart sound detector 555 detects a type of heart sounds and presents a timing trend related to the detected heart sounds on display 341. In a further embodiment, the user observes the presented trend to confirm its accuracy.

For phonocardiographic image-based diagnostic purpose, diagnosing cardiac condition at 880 includes, in one embodiment, diagnosing a cardiac condition at 982 based on whether that type of heart sounds has been identified from the phonocardiographic image at 972. The presence or absence of certain heart sounds or heart sound components indicate existence of a cardiac condition. In one embodiment, the user makes a diagnosis of heart failure based on the existence of the third heart sound, S3. In one specific embodiment, as illustrated in FIG. 7, heart sound S3 is present during the non-paced cardiac cycles (associated with the AVI) but diminishes during most of the paced cardiac cycles (Associated with the AVDs). This indicates that the patient has heart failure treatable by cardiac pacing. In another embodiment, diagnosing cardiac condition at 880 includes diagnosing a cardiac condition at 984 based on the timing trend of the identified heart sound observed or detected at 974. An abnormal timing trend indicates a deteriorated myocardium and/or an abnormal electrical conduction system that are associated with poor hemodynamic performance. In one embodiment, the user examines the efficacy of a cardiac therapy in treating heart failure based on a trend of the interval between the atrial depolarization and the first heart sound. In one specific embodiment, as illustrated in FIG. 7, the Asense-S1 interval is shortened during the paced cardiac cycles associated with AVD1, AVD2, and AVD3, indicating that pacing at these AVDs is effective in shortening the interval between the atrial depolarization and the first heart sound, which is indicative of the electromechanical interval between atrial depolarization and mitral valve closure.

Figure 10:
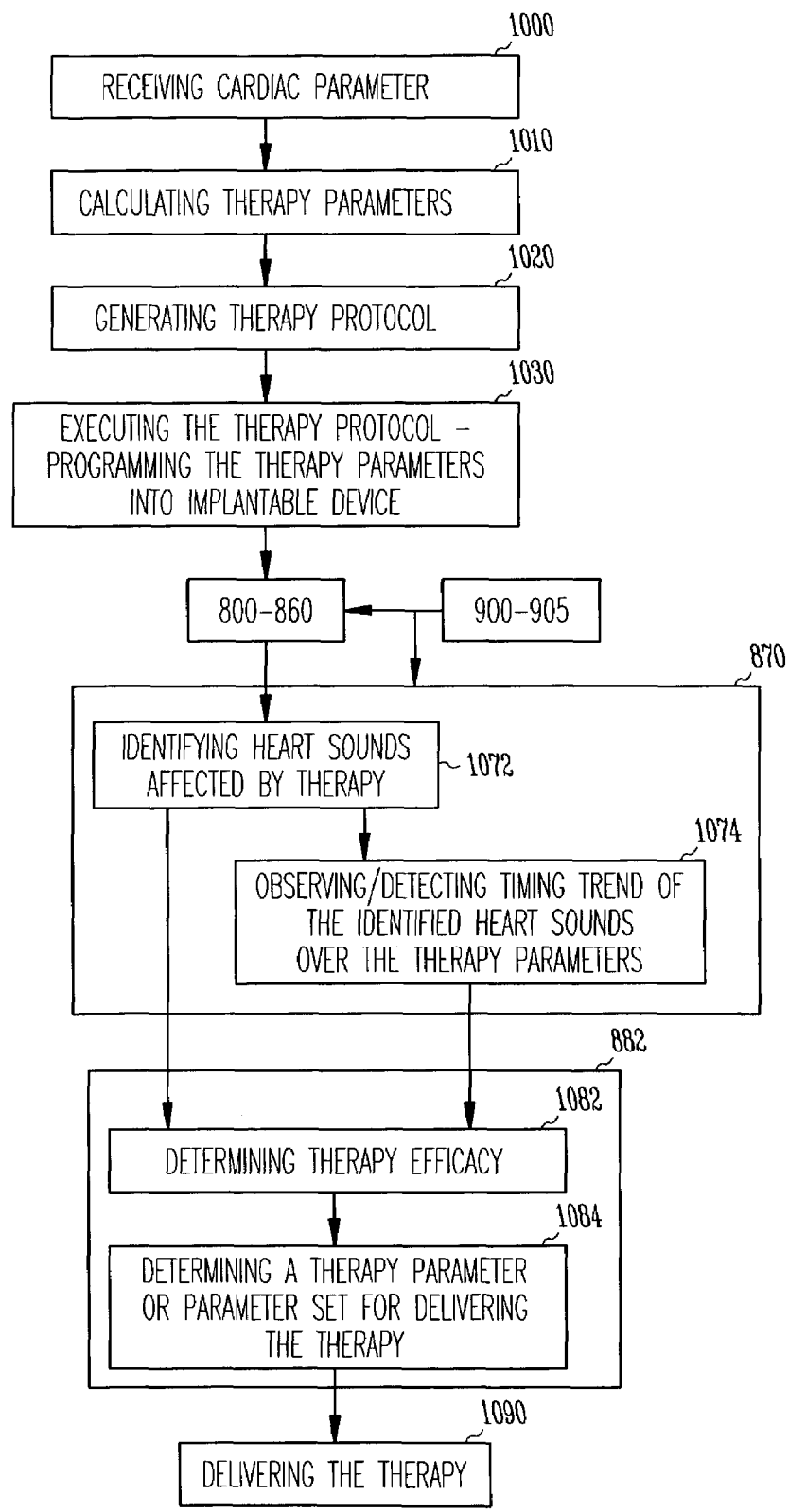
FIG. 10 is a flow chart illustrating one embodiment of a method for phonocardiographic image-based therapy evaluation.

FIG. 10 is a flow chart illustrating one embodiment of a method for phonocardiographic image-based therapy evaluation. One of the applications of the phonocardiographic image such as phonocardiographic image 780 is to provide means for determining a suitable therapy treating a cardiac condition. In one embodiment, the phonocardiographic image provides for an overall visual presentation of results of a therapy evaluation. In one embodiment, as illustrated in FIG. 10, the therapy evaluation provides for indications of whether a therapy is effective and an approximately optimal therapy parameter.

The method for acquiring and presenting the phonocardiographic image, including steps 800–880 discussed above with reference to FIG. 8, is incorporated into the method for the phonocardiographic image-based therapy evaluation. In one embodiment, programmer 140, and specifically therapy controller 360 discussed above with reference to FIG. 6, performs steps 1000–1030 on an automatic basis. At 1000, cardiac parameter input 662 receives at least one cardiac parameter related to a patient. In one embodiment, the user enters the cardiac parameter. In another embodiment, signal processor 350 measures the cardiac parameter from the cardiac signals and/or event markers telemetered from implanted device 110. At 1010, therapy parameter calculator 663 calculates a series of therapy parameters or parameter sets based on the cardiac parameter. At 1020, a therapy protocol including descriptions of a sequence of therapies is generated. The therapies each include a parameter set defining the therapy using one of the calculated therapy parameter or parameter set. At 1030, therapy parameter sequencing module 669 executes the therapy protocol by sending the therapy descriptions to implanted device 110 via telemetry link 170, one portion (description of one of the sequence of therapies) at a time, as timed by timer 668. The calculated therapy parameters or parameter sets are each tested during the protocol execution.

In an alternative embodiment, the user manually performs steps 1000–1030 or portions thereof. At 1000, the user measures or otherwise obtains at least one cardiac parameter related to a patient. At 1010, the user calculates therapy parameters or parameter sets based on the cardiac parameter. At 1020, the user generates a therapy protocol containing therapy descriptions of a sequence of therapies each including one of the calculated therapy parameters or parameter sets. At 1030, the user sends the therapy descriptions to implanted device 110 by manually entering commands into user input module 342 of programmer 140, one portion (description of one of the sequence of therapies) at a time, with intervals between sending the portions of the therapy descriptions timed by the user. In one embodiment, the user enters changes of therapy parameters or parameter sets and causes programmer 140 to send the changed therapy parameters or parameter sets to implanted device 110 such that each therapy parameter or parameter set calculated at 1010 are tested.

The phonocardiograph session discussed with reference to FIG. 8 starts any time after the therapy protocol execution (1030) begins. In one embodiment, the phonocardiograph session starts at approximately the same time when therapy protocol execution (1030) begins. In another embodiment, the phonocardiograph session starts after the therapy protocol execution (1030) ends. In a further embodiment, the phonocardiograph session is performed, by using programmer 140, after the completion of the therapy protocol execution (1030). In an alternative embodiment, the phonocardiograph session is performed, by using a computer in which signal processor 350 is installed, after the completion of the therapy protocol execution (1030).

For purposes of the phonocardiographic image-based therapy evaluation, observing the phonocardiographic image at 870 includes identifying heart sounds possibly affected by the therapy at 1072. In one embodiment, this includes identifying a particular type of heart sounds as predetermined by a purpose for the therapy evaluation. In one embodiment, observing the phonocardiographic image at 870 further includes observing or detecting a timing trend of the identified heart sounds at 1074. In one embodiment, the user observes the trend of an interval between a type of cardiac events and the identified type of heart sounds. In another embodiment, heart sound detector 555 detects a type of heart sounds and presents a timing trend related to the detected heart sounds on display 341. In a further embodiment, the user observes the presented trend to confirm its accuracy.

For purposes of the phonocardiographic image-based therapy evaluation, determining a cardiac therapy at 882 includes determining the cardiac therapy based on an outcome of observing the phonocardiographic image at 870. In one embodiment, determining the cardiac therapy at 882 includes determining, at 1082, an efficacy of each of the evaluated therapies, based on whether the therapy is observed to affect a presence of the type of heart sounds to be identified at 1072 and/or the trend of the type of heart sounds observed or detected at 1074. In a further embodiment, if it is determined at 1082 that the therapy is to be delivered, determining the cardiac therapy at 882 includes determining a therapy parameter of parameter set at 1084, based on the effect of the tested therapy parameters or parameter sets on the presence of the type of heart sounds to be identified at 1072 and/or the trend of the type of heart sounds observed or detected at 1074. In one embodiment, this includes selecting one of the tested therapy parameters or parameter sets. In another embodiment, this includes determining a therapy parameter or parameter set based on the presence of the type of heart sounds to be identified at 1072 and/or the trend of the type of heart sounds observed or detected at 1074.

At 1090, if it is determined at 1082 that the therapy is to be delivered, the therapy is delivered to the patient, with the one parameter or parameter set determined at 1084. In one embodiment, this includes programming the parameters or parameter sets to implantable device 110 using programmer 140. The parameter or parameter set is then stored in the memory circuit of implant controller 323. In one further embodiment, the method of phonocardiographic image-based therapy evaluation is repeated on a predetermined schedule. In another further embodiment, the method for phocardiographic image-based therapy evaluation is repeated on a needy basis, as determined by the user. If the repeated phonocardiographic image-based therapy evaluation results in a new parameter or parameter set, this new parameter or parameter set is programmed into implanted device 110 to replace the parameter or parameter set stored in the memory circuit of implant controller 323.

Figure 11:
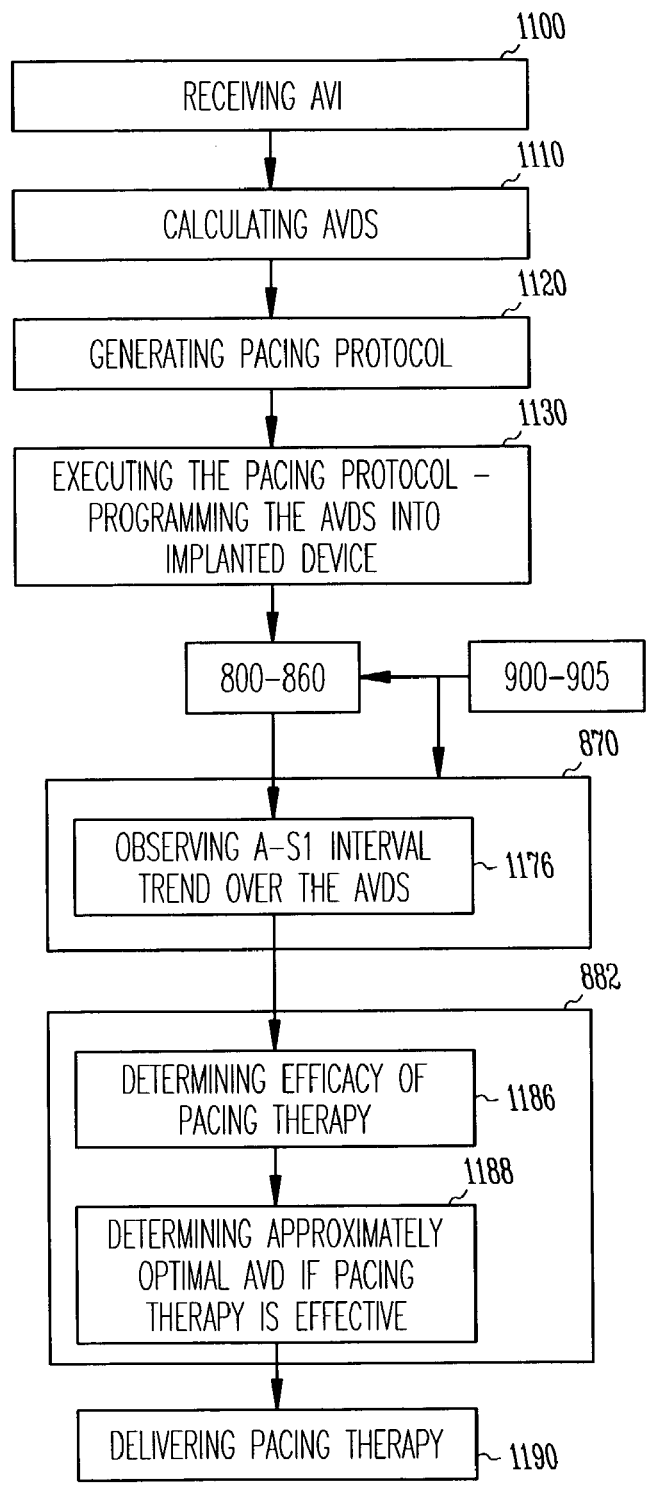
FIG. 11 is a flow chart illustrating one specific embodiment of a method for phonocardiographic image-based AVD optimization.

FIG. 11 is a flow chart illustrating one embodiment of a method for phonocardiographic image-based AVD optimization. This embodiment provides for an example of the method for phonocardiographic image-based therapy evaluation discussed above with reference to FIG. 10. Other applications includes, by way of example, but not by way of limitation, determination or optimization of pacing site or sites, pacing mode, and other pacing interval or delay parameters.

In the embodiment illustrated in FIG. 11, the phonocardiographic image such as phonocardiographic image 780 provides for means for determining an approximately optimal AVD based on a pacing therapy evaluation. The approximately optimal AVD is an AVD associated with an approximately optimal hemodynamic performance as indicated by one or more heart sounds. The phonocardiographic image provides for a visual presentation of results associated with all AVDs tested during one therapy (pacing) protocol execution.

The method for acquiring and presenting the phonocardiographic image, including steps 800–880 discussed above with reference to FIG. 8, is incorporated into the method for the phonocardiographic image-based AVD optimization. In one embodiment, programmer 140, and specifically therapy controller 360 discussed above with reference to FIG. 6, performs steps 1100–1130 on an automatic basis. At 1100, cardiac parameter input 662 receives an intrinsic AVI measured from the patient. In one embodiment, the user enters the AVI, which is previously measured, through user input module 342. In another embodiment, signal processor 350 measures the AVI from event markers telemetered from implanted device 110. At 1110, therapy parameter calculator 663 calculates values of a predetermined number of AVDs based on the AVI. In one embodiment, the number of AVDs to be evaluated depends on a compromise between time required for the pacing therapy evaluation and a degree of accuracy in identifying an optimal AVD. In one embodiment corresponding to the illustration of FIG. 7, five AVDs, AVD1–AVD5, are calculated based on the AVI. In one specific embodiment, AVD1–AVD5 are evenly spaced, with AVD1 near zero and AVD5 near the AVI. In another specific embodiment, AVD1–AVD5 are evenly spaced, AVD1 is about 25 ms, and AVD5 is about 30 ms shorter than the AVI. At 1120, a pacing protocol including descriptions of a sequence of pacing therapies is generated. In one embodiment, the pacing therapies include VDD mode pacing therapies each including one of the calculated AVDs. In one embodiment, the pacing therapies include DDD mode pacing therapies each including one of the calculated AVDs. At 1130, therapy parameter sequencing module 669 executes the pacing protocol by sending the therapy descriptions to implanted device 110 via telemetry link 170, one portion (description of one of the therapies) at a time, as timed by timer 668. The calculated AVDs are each tested during the protocol execution.

The phonocardiograph session discussed with reference to FIG. 8 starts any time after the pacing protocol execution (at 1130) begins. In one embodiment, the phonocardiograph session starts at approximately the same time when pacing protocol execution (at 1130) begins. In another embodiment, the phonocardiograph session starts after the therapy protocol execution (at 1130) ends. In a further embodiment, the phonocardiograph session is performed after the completion of the therapy protocol execution (at 1130) by using programmer 140. In an alternative embodiment, the phonocardiograph session is performed after the completion of the therapy protocol execution (1130) by using a computer in which signal processor 350 is installed.

For purposes of the phonocardiographic image-based AVD optimization, observing the phonocardiographic image at 870 includes observing a trend of a heart sound over the tested AVDs and the AVI at 1176. In one specific embodiment, referring to FIG. 7, this includes observing a trend of the interval (A-S1 interval, or $T_{A-S1}$) between atrial event Asense and heart sound S1 over the AVI and AVD1–AVD5. The A-S1 interval trend indicates the trend of the electromechanical interval between the atrial contraction and the mitral valve closure over non-pacing (at AVI) and pacing at AVD1–AVD5. In one embodiment, the A-S1 interval is referred to as P-S1 interval because Asense marks represent detected P-waves indicative of intrinsic atrial depolarization. In another embodiment, the A-S1 interval also includes the interval between delivery of an atrial pacing pulse (Apace) and heart sound S1.

For purposes of the phonocardiographic image-based AVD optimization, determining a pacing therapy at 882 includes determining the approximately optimal AVD based on an outcome of observing the phonocardiographic image at 870. In one embodiment, determining the pacing therapy at 882 includes determining whether the pacing therapy evaluation shows that at least one of the AVDs is associated with a significant improvement the patient's hemodynamic performance as indicated by a heart sound trend. In a further embodiment, if it is determined at 1186 that at least one of the AVDs is associated with a significant improvement the patient's hemodynamic performance, determining the cardiac therapy at 882 includes determining the approximately optimal AVD at 1188. In one embodiment, this includes determining the approximately optimal AVD based on the A-S1 interval trend over the tested AVDs. In another embodiment, this includes determining the approximately optimal AVD by selecting one of the tested AVDs based on the A-S1 interval trend over the tested AVDs. In one embodiment, as discussed below with reference to FIG. 12 and FIG. 13, determining the pacing therapy at 882 includes determining an approximately optimal AVD for maximizing ventricular contractility by using the phonocardiographic image.

At 1190, if it is determined at 1186 that the pacing therapy is effective, the pacing therapy is delivered to the patient, with the approximately optimal AVD determined at 1188. In one embodiment, this includes programming the approximately optimal AVD into implanted device 110 using programmer 140. In one embodiment, the approximately optimal AVD is programmed into implanted device 110, and is then stored in the memory circuit of implant controller 323. In one further embodiment, the method of phonocardiographic image-based AVD optimization is repeated on a predetermined schedule. In another further embodiment, the method of phonocardiographic image-based AVD optimization is repeated on a needy basis, as determined by the user. If the repeated phonocardiographic image-based AVD optimization results in a new approximately optimal AVD, this new approximately optimal AVD is programmed into implanted device 110 to replace the AVD stored in the memory circuit of implant controller 323.

Figure 12:
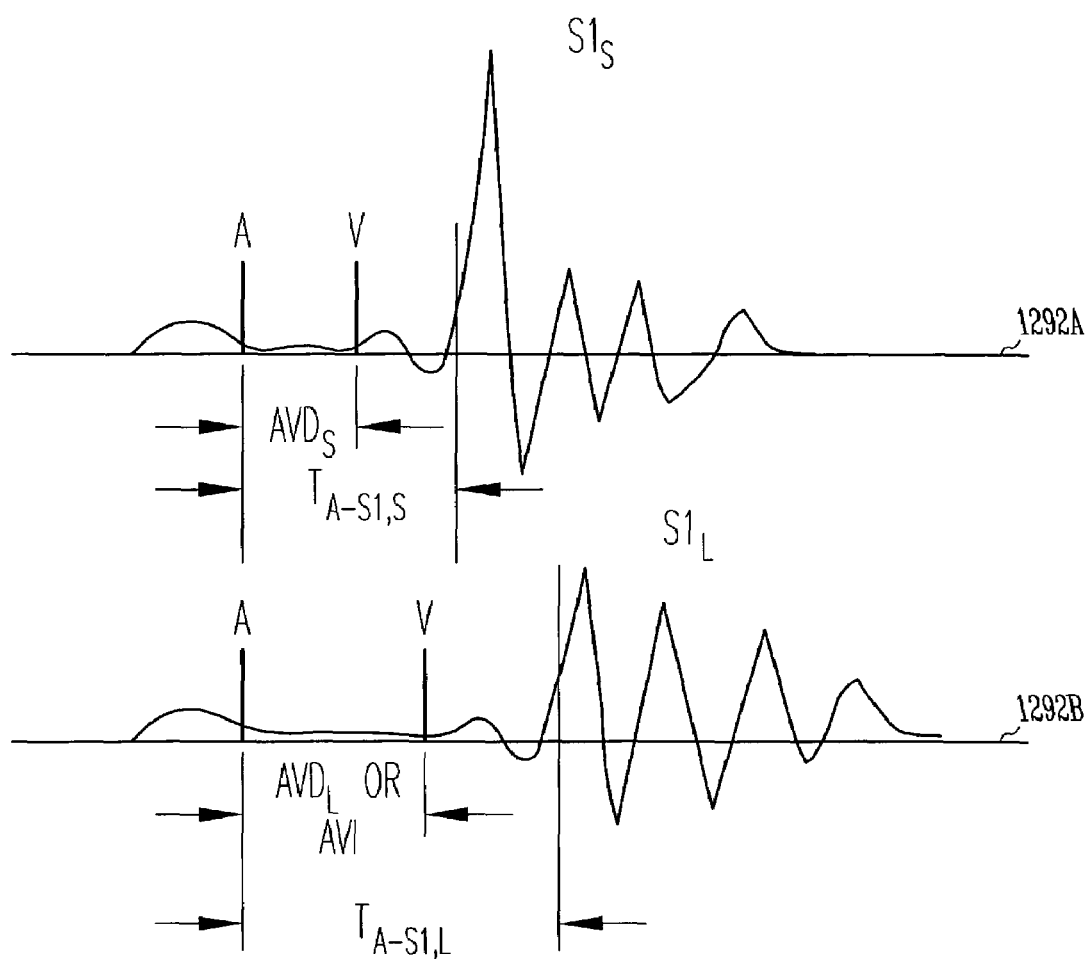
FIG. 12 is an illustration of one embodiment of a method for AVD optimization for maximum ventricular contractility.

FIG. 12 is an illustration of one embodiment of a method for AVD optimization for maximum ventricular contractility. One strategy optimizing hemodynamic performance with CRT is to maximize ventricular contractility. One measure of ventricular contractility is the maximum rate of ventricular pressure increase, $dP/dt_{max}$, during isovolumic contraction. Direct measurement of dP/dt requires intraventricular catheterization with a pressure transducer. On the other hand, it has been observed that the timing of certain heart sounds correlates to the strength of heart contraction. Thus, heart sound timing is capable of being a surrogate measure of relative dP/dt changes that does not require an intraventricular pressure sensor. It is believed that ventricular contractility is maximized when the onset of S1 due to pacing coincides with the intrinsic S1 to achieve the best fusion of paced and intrinsic activations.

FIG. 12 illustrates an acoustic sensor signal segment 1292A and another acoustic sensor signal segment 1292B each indicative of S1. Cardiac events A (sensed or paced atrial events) and V (sensed or paced ventricular events) are marked on both acoustic sensor signal segments. Acoustic sensor signal segment 1292A is associated with ventricular pacing at a relatively short AVD, $AVD_S$, and including $S1_S$ due to the pacing at $AVD_S$. The A-S1 interval, $T_{A-S1,S}$, indicates the S1 timing associated with pacing. Acoustic sensor signal segment 1292B is associated with an intrinsic ventricular contraction or ventricular pacing at a relatively long AVD, $AVD_L$, and including $S1_L$, which is the intrinsic S1. The A-S1 interval, $T_{A-S1,L}$, indicates the intrinsic S1 timing not affected by pacing. To achieve an approximately maximum ventricular contractility, a ventricular pacing pulse is delivered to cause approximately simultaneous paced and intrinsic activations. The approximately optimal AVD is an AVD at with the ventricular pacing minimally shortens the intrinsic A-S1 interval.

Figure 13:
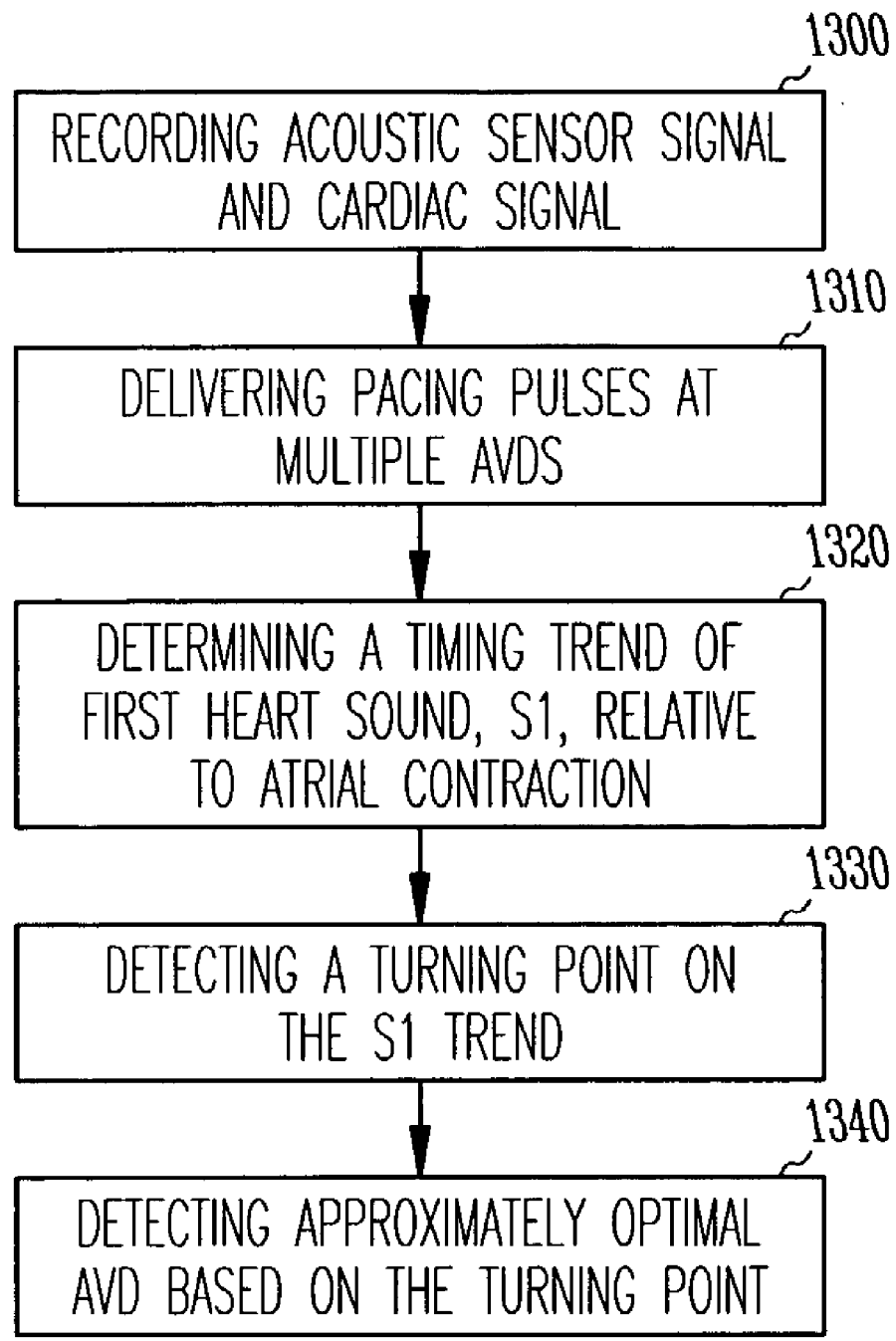
FIG. 13 is a flow chart illustrating one embodiment of a method for phonocardiographic image-based AVD optimization for maximum ventricular contractility.

FIG. 13 is a flow chart illustrating one embodiment of a method for phonocardiographic image-based AVD optimization for maximum ventricular contractility. At 1300, an acoustic sensor signal indicative of S1 is recorded. A cardiac signal indicative of cardiac events A (sensed or paced atrial events) and V (sensed or paced ventricular events) is also recorded. Ventricular pacing pulses at a plurality of AVDs are delivered while the acoustic sensor signal and cardiac signal are recorded at 1310. In one embodiment, the pacing pulses are delivered by executing a pacing protocol that is discussed above with reference to FIG. 11. At 1320, an S1 timing trend is determined as a curve indicating the beginning of S1 relative to cardiac event A. In one embodiment, the acoustic sensor signal is presented as the phonocardiographic image, which includes acoustic sensor signal segments aligned by cardiac event A, and the S1 timing trend is observed from the phonocardiographic image. At 1330, a turning point ("knee") is detected from the S1 timing trend. The knee represents a point at which the A-S1 interval begins to shorten as a result of pacing. In one embodiment, the S1 timing trend is a curve indicating the beginning of heart sound S1 on the stacked acoustic sensor signal segments of the phonocardiographic image. In one embodiment, heart sound detector 555 detects the leading edge of the first heart sounds and presents it on display 341. In a further embodiment, the user observes the detected leading edge of the first heart sounds to confirm its accuracy before locating the turning point. At 1340, an approximately optimal AVD is determined as the longest AVD, among the tested plurality of AVDs, at the knee. In other words, the approximately optimal AVD is the longest AVD associated with a visibly shortened A-S1 interval.

Figure 14:
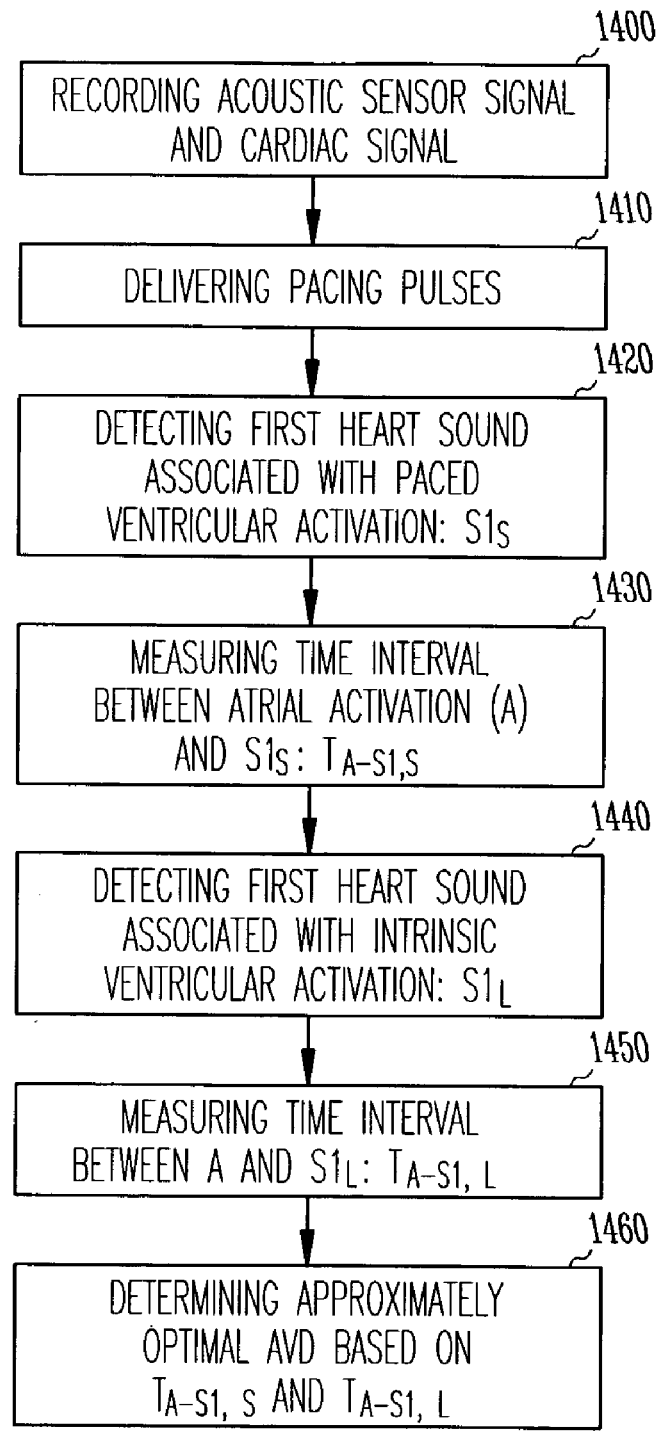
FIG. 14 is a flow chart illustrating one embodiment of another method for phonocardiographic image-based AVD optimization for maximum ventricular contractility.

FIG. 14 is a flow chart illustrating one embodiment of another method for phonocardiographic image-based AVD optimization for maximum ventricular contractility. At 1400, an acoustic sensor signal indicative of S1 sounds is recorded. A cardiac signal indicative of atrial and ventricular electrical events is also recorded. Ventricular pacing pulses are delivered while the acoustic sensor signal and cardiac signal are recorded at 1410. The acoustic sensor signal includes indications of S1 associated with paced ventricular activation and S1 associated with intrinsic ventricular activation. S1 associated with the paced ventricular activations are observed at AVDs that are sufficient short such that the ventricular pacing visibly shortens the A-S1 interval. S1 associated with the intrinsic ventricular activations are observed when ventricular pacing is not delivered or at AVDs that are sufficiently long such that the ventricular pacing does not visibly shortens the A-S1 interval. In one embodiment, the pacing pulses are delivered by executing a pacing protocol that is discussed above with reference to FIG. 11. At 1420, an S1 associated with a paced ventricular activation, $S1_S$, is detected. At 1430, a short A-S1 interval, $T_{A-S1,S}$, is measured between a cardiac event A and $S1_S$, where $S1_S$ is adjacently subsequent to cardiac event A. At 1440, an S1 associated with an intrinsic ventricular activation, $S1_L$, is detected. At 1450, a long A-S1 interval, $T_{A-S1,L}$, is measured between a cardiac event A and $S1_L$, where $S1_L$ is adjacently subsequent to cardiac event A. In one embodiment, steps 1420–1450 are performed based on a display of acoustic sensor signal such as the phonocardiographic image. In one specific embodiment, $S1_S$ is one of the S1 sounds observed to be associated with the shortest A-S1 interval, typically seen with the shortest AVD, and $S1_L$ is one of the S1 sounds observed to be associated with the longest A-S1 interval, typically seen with AVI (non-paced cardiac cycles) as well as the longest AVD. In one embodiment, the user measures the A-S1 intervals on the phonocardiographic image with the electronic caliper of user input module 342. In another embodiment, signal processor 350 measures the A-S1 intervals automatically. In one embodiment, each A-S1 interval is measured between the cardiac event A and the beginning of heart sound S1. In one specific embodiment, cardiac event A is represented by an atrial event marker. At 1460, the approximately optimal AVD is determined by using a formula:

$$AVD_{OPT}=AVD_S+T_{A-S1,L}-T_{A-S1,S},$$

where the $AVD_{OPT}$ is the approximately optimal AVD, and the $AVD_S$ is the AVD associated with the detected $S1_S$.

In a specific embodiment combining methods illustrated in FIG. 7 (phonocardiographic image 780), FIG. 11 (pacing protocol with AVD1–AVD5), FIG. 13, and FIG. 14, $S1_S$ is detected at AVD1, and $S1_L$ is detected at AVD5. The user measures A-S1 intervals associated with AVD1 and AVD5. The approximately optimal AVD is determined as:

$$AVD_{OPT}=AVD1+T_{A-S1,AVD5}-T_{A-S1,AVD1},$$

where the $T_{A-S1,AVD5}$ is the $T_{A-S1}$ corresponding to AVD5 (the longest AVD), and the $T_{A-S1,AVD1}$ is the $T_{A-S1}$ corresponding to AVD1 (the shortest AVD).

In a further embodiment, a first estimate of the approximately optimal AVD is determined based on results of executing a first pacing protocol including a predetermined number of "coarsely spaced" AVDs. The method of AVD optimization is repeated, with another predetermined number of "finely spaced" AVDs having values near the first estimate used to generate a second protocol. The approximately optimal AVD is then determined based on the results of executing the second pacing protocol. In one embodiment, the "coarsely spaced" AVDs are evenly distributed within a first time interval range being a predetermined fraction of the AVI. The "finely spaced" AVDs are evenly distributed within a second time interval range that is a predetermined fraction of the first time interval range. The second time interval range includes the calculated $AVD_{OPT}$. In one specific embodiment, the second time interval range centers at the calculated $AVD_{OPT}$. Both the first estimate and the final approximately optimal AVD is determined by the "knee" detection method discussed with reference to FIG. 13, the $AVD_{OPT}$ formula discussed with reference to FIG. 14, or a combination of both. More than one repetition can be performed as necessary or desired. This embodiment requires more time but likely results in an approximately optimal AVD that is closer to the AVD associated with the optimal hemodynamic performance. In a specific embodiment, the first estimate of the approximately optimal AVD is determined by using the $AVD_{OPT}$ formula above, after generating and executing the first pacing protocol including the predetermined number of "coarsely spaced" AVDs. The approximately optimal AVD is then determined by locating a knee in the leading edge of the first heart sounds (S1 timing trend) in the phonocardiographic image resulted from executing the second pacing protocol. The knee corresponds to the approximately optimal AVD, which is the longest AVD (among the finely spaced AVDs) associated with a visibly shortened A-S1 interval ($T_{A-S1}$).

It is to be understood that the above detailed description is intended to be illustrative, and not restrictive. For example, the phonocardiographic image can be formed with a cardiac signal and an acoustic sensor signal acquired by any implanted or external medical device providing for ECG and heart sound monitoring. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A system for applying pacing pulses to a heart, the system comprising:
   a sensing circuit to sense a cardiac signal;
   a therapy circuit to deliver the pacing pulses;
   an acoustic sensor to produce an acoustic sensor signal indicative of heart sounds;
   a controller coupled to the therapy circuit, the controller including:
      a therapy protocol synthesizer adapted to generate a sequence of pacing parameters; and
      an automatic therapy protocol execution module adapted to time pacing pulse deliveries each associated with one parameter of the sequence of pacing parameters; and
   a processor coupled to the sensing circuit, the acoustic sensor, and the controller, the processor including an image formation module adapted to produce a phonocardiographic image based on the cardiac signal and the acoustic sensor signal, the phonocardiographic image including a stack of segments of the acoustic sensor signal aligned by a selected type of the cardiac events and grouped by at least parameters of the sequence of pacing parameters.

2. The system of claim 1, wherein the acoustic sensor includes an accelerometer to sense an acceleration signal indicative of the heart sounds.

3. The system of claim 1, wherein the acoustic sensor includes a microphone to sense the heart sounds.

4. The system of claim 1, further comprising a display, coupled to the processor, to present the phonocardiographic image.

5. The system of claim 4, wherein the processor includes:
   a signal segmenting module coupled to the sensing circuit and the acoustic sensor, the signal segmenting module adapted to segment the acoustic sensor signal into acoustic sensor signal segments based on the selected type of the cardiac events;
   a signal alignment module coupled to the signal segmenting module, the signal alignment module adapted to temporally align the acoustic sensor signal segments by the selected type of the cardiac events; and
   a signal grouping module coupled to the signal alignment module, the signal grouping module adapted to sort and group the acoustic sensor signal segments according to a grouping instruction.

6. The system of claim 5, wherein the signal grouping module comprises a signal segment averaging module adapted to average selected segments of the acoustic sensor signal segments according to the grouping instruction.

7. The system of claim 5, furthering comprising a user input module, coupled to the display and the processor, to receive at least one of a user command selecting the selected type of the cardiac events and the group instruction.

8. The system of claim 5, wherein the processor further includes a heart sound detector coupled to the signal grouping module, the heart sound detector adapted to detect at least one selected type of heart sounds and present representations of the detected heart sounds on the phonocardiographic image.

9. The system of claim 5, wherein the therapy protocol synthesizer includes a therapy parameter calculator adapted to calculate the sequence of pacing parameters from a measured cardiac time interval.

10. The system of claim 9, wherein the therapy protocol synthesizer includes a therapy parameter calculator adapted to calculate a sequence of atrioventricular delays (AVDs) based on an intrinsic atrioventricular interval (AVI).

11. A cardiac rhythm management system, comprising:
    an implantable device including:
       a sensing circuit to sense a cardiac signal; and
       a therapy circuit to deliver pacing pulses;
    an acoustic sensor to produce an acoustic sensor signal indicative of heart sounds; and
    an external programmer communicatively coupled to the implantable device and the acoustic sensor, the external programmer including:
       a controller communicatively coupled to the therapy circuit, the controller including:
          a therapy protocol synthesizer adapted to generate a sequence of pacing parameters; and
          an automatic therapy protocol execution module adapted to time pacing pulse deliveries each associated with one parameter of the sequence of pacing parameters; and
       a processor communicatively coupled to the sensing circuit, the acoustic sensor, and the controller, the processor including an image formation module adapted to produce a phonocardiographic image based on the cardiac signal and the acoustic sensor signal, the phonocardiographic image including a stack of segments of the acoustic sensor signal aligned by a selected type of the cardiac events and grouped by at least parameters of the sequence of pacing parameters.

12. The system of claim 11, wherein the acoustic sensor includes an implantable acoustic sensor electrically connected to the implantable device.

13. The system of claim 11, wherein the acoustic sensor includes an external acoustic sensor electrically connected to the external programmer.

14. The system of claim 11, wherein the external programmer further includes a display, coupled to the processor, to present the phonocardiographic image.

15. The system of claim 11, wherein the processor includes:
    a signal segmenting module coupled to the sensing circuit and the acoustic sensor, the signal segmenting module adapted to segment the acoustic sensor signal into acoustic sensor signal segments based on the selected type of the cardiac events;
    a signal alignment module coupled to the signal segmenting module, the signal alignment module adapted to temporally align the acoustic sensor signal segments by the selected type of the cardiac events; and
    a signal grouping module coupled to the signal alignment module, the signal grouping module adapted to sort and group the acoustic sensor signal segments according to a grouping instruction.

16. The system of claim 15, wherein the signal grouping module comprises a signal segment averaging module adapted to average selected segments of the acoustic sensor signal segments according to the grouping instruction.

17. The system of claim 15, wherein the external programmer further includes a user input module, coupled to the display and the processor, to receive at least one of a user command selecting the selected type of the cardiac events and the grouping instruction.

18. The system of claim 15, wherein the processor further includes a heart sound detector coupled to the signal grouping module, the heart sound detector adapted to detect at least one selected type of heart sounds and present representations of the detected heart sounds on the phonocardiographic image.

19. The system of claim 15, wherein the therapy protocol synthesizer includes a therapy parameter calculator adapted to calculate the sequence of pacing parameters from a measured cardiac time interval.

20. The system of claim 19, wherein the therapy protocol synthesizer includes a therapy parameter calculator adapted to calculate a sequence of atrioventricular delays (AVDs) based on an intrinsic atrioventricular interval (AVI).

21. A method for apply pacing pulses to a heart, the method comprising:
  generating a first sequence of atrioventricular delays (AVDs);
  delivering a first sequence of pacing pulses each associated with one AVD of the first sequence of AVDs;
  receiving a cardiac signal indicative of cardiac events during the delivering the first sequence of pacing pulses;
  receiving an acoustic sensor signal indicative of heart sounds during the delivering the first sequence of pacing pulses; and
  forming a phonocardiographic image based on the cardiac signal and the acoustic sensor signal, the phonocardiographic image including a stack of segments of the acoustic sensor signal aligned by a selected type of the cardiac events and grouped by at least the first sequence of AVDs; and
  presenting the phonocardiographic image.

22. The method of claim 21, wherein receiving the cardiac signal comprises receiving event markers representing the cardiac events, and wherein the selected type of the cardiac events are identified by a corresponding type of the event markers.

23. The method of claim 21, wherein receiving the acoustic sensor signal comprises receiving an acceleration signal.

24. The method of claim 21, wherein receiving the acoustic sensor signal comprises receiving a microphone signal.

25. The method of claim 21, further comprising detecting from the phonocardiographic image a trend related to a predetermined type of the heart sounds over at least the first sequence of AVDs.

26. The method of claim 25, further comprising determining an approximately optimal AVD based on the trend and the first sequence of AVDs.

27. The method of claim 21, further comprising measuring an intrinsic atrioventricular interval (AVI), and wherein generating the first sequence of AVDs comprises calculating the first sequence of AVDs based on the intrinsic AVI.

28. The method of claim 27, wherein presenting the phonocardiographic image comprises presenting the phonocardiographic image including the segments of the acoustic sensor signal aligned by atrial events and grouped by the first sequence of AVDs and the intrinsic AVI.

29. The method of claim 28, further comprising observing the phonocardiographic image to identify a timing trend of the first heart sound (S1) over the first sequence of AVDs and the AVI; and
  determining the approximately optimal AVD based on the timing trend of S1.

30. The method of claim 29, wherein identifying the timing trend of S1 comprises detecting a beginning of each of the first heart sounds.

31. The method of claim 29, wherein determining the approximately optimal AVD comprises locating a tuning point in the timing trend of S1, the tuning point corresponding to the approximately optimal AVD being a shortest AVD of the first sequence of AVDs at which a time interval $T_{A\text{-}S1}$ between an atrial event (A) and the first heart sound (S1) begins to substantially decrease in response to the delivering the first sequence of pacing pulses.

32. The method of claim 31, wherein calculating the first sequence of AVDs based on the intrinsic AVI comprises calculating a predetermined number of AVDs evenly distributed within a first time interval range being a first predetermined fraction of the intrinsic AVI.

33. The method of claim 28, further comprising observing the phonocardiography to identify a trend of a time interval $T_{A\text{-}S1}$ between an atrial event (A) and the first heart sound (S1) over the first sequence of AVDs and the AVI; and
  determining the approximately optimal AVD based on the trend of $T_{A\text{-}S1}$.

34. The method of claim 33, wherein determining the approximately optimal AVD comprises:
  measuring a $T_{A\text{-}S1,AVDS}$ being a $T_{A\text{-}S1}$ associated with the shortest AVD ($AVD_S$) among the first sequence of AVDs;
  measuring a $T_{A\text{-}S1,AVDL}$ being a $T_{A\text{-}S1}$ associated with the longest AVD ($AVD_L$) among the first sequence of AVDs;
  calculating the approximately optimal AVD based on:

$$AVD_{OPT} = AVD_S + T_{A\text{-}S1,AVDL} - T_{A\text{-}S1,AVDS}.$$

35. The method of claim 34, wherein calculating the first sequence of AVDs based on the intrinsic AVI comprises calculating a predetermined number of AVDs evenly distributed within a first time interval range being a first predetermined fraction of the intrinsic AVI.

36. The method of claim 35, wherein:
  generating the first sequence of AVDs further comprises generating a second sequence of AVDs evenly distributed within a second time interval range being a predetermined fraction of the first time interval range and including the calculated approximately optimal AVD ($AVD_{OPT}$); and
  delivering the first sequence of pacing pulses further comprises delivering a second sequence of pacing pulses each associated with one AVD of the second sequence of AVDs; and further comprising:
  observing the phonocardiographic image to identify a timing trend of the first heart sound (S1) over the second sequence of AVDs and the AVI; and
  determining a further approximately optimal AVD by locating a tuning point in the timing trend of S1, the tuning point corresponding to the further approximately optimal AVD being a shortest AVD of the first sequence of AVDs at which $T_{A\text{-}S1}$ begins to substantially decrease in response to the delivering the second sequence of pacing pulses.

37. A method comprising;
receiving an acoustic sensor signal indicative of an intrinsic heart sound associated with an intrinsic ventricular contraction adjacently subsequent to a first atrial contraction and a paced heart sound associated with a paced ventricular contraction adjacently subsequent to a second atrial contraction;
receiving a cardiac signal temporally associated with the acoustic sensor signal, the cardiac signal indicative of the first and second atrial contractions;
measuring a first time interval between the first atrial contraction and the intrinsic heart sound;
measuring a second time interval between the second atrial contraction and the paced heart sound; and
determining an approximately optimal pacing therapy based on the first and second time intervals.

38. The method of claim 37, wherein:
receiving the acoustic sensor signal comprises receiving the acoustic sensor signal indicative intrinsic first heart sound $S1_L$ and paced first heart sound $S1_S$, $S1_S$ associated with an atrioventricular delay, $AVD_S$;
measuring the first time interval comprises measuring the first time interval, $T_{A-S1,S}$, between the first atrial activation and $S1_S$;
measuring the second time interval comprises measuring the second time interval, $T_{A-S1,L}$, between the second atrial activation and $S1_L$; and
determining an approximately optimal pacing therapy comprises determining an approximately optimal atrioventricular delay, $AVD_{OPT}$, for maximizing ventricular contractility, based on $T_{A-S1,S}$ and $T_{A-S1,L}$.

39. The method of claim 38, wherein determining $AVD_{OPT}$ comprises using the formula:

$$AVD_{OPT} = AVD_S + T_{A-S1,L} - T_{A-S1,S}.$$

40. The method of claim 39, wherein:
receiving the cardiac signal comprises receiving first and second event markers representing the first and second atrial contractions, respectively;
measuring the first time interval comprises measuring the first time interval, $T_{A-S1,S}$, between the first event marker and $S1_S$; and
measuring the second time interval comprises measuring the second time interval, $T_{A-S1,L}$, between the second event marker and $S1_L$.

41. The method of claim 40, furthering comprising presenting a phonocardiographic image formed based on the cardiac signal and the acoustic sensor signal, the phonocardiographic image including a stack of segments of the acoustic sensor signal aligned by the atrial contractions and grouped by at least the intrinsic and paced ventricular activations, and wherein:
measuring $T_{A-S1,S}$ includes detecting $S1_S$ on the phonocardiographic image and measuring $T_{A-S1,S}$ on the phonocardiographic image; and
measuring $T_{A-S1,L}$ includes detecting $S1_L$ on the phonocardiographic image and measuring $T_{A-S1,L}$ on the phonocardiographic image.

42. A system for applying pacing pulses to a heart, the system comprising:
means for producing an acoustic sensor signal indicative of heart sounds;
means for delivering pacing pulses associated with a predetermined sequence of pacing parameters; and
means for producing a phonocardiographic image based on selected type cardiac events and the acoustic sensor signal, the phonocardiographic image including a stack of segments of the acoustic sensor signal aligned by the selected type cardiac events and grouped by at least parameters of the predetermined sequence of pacing parameters.

43. The system of claim 42, further comprising means for displaying the cardiophonographic image.

44. The system of claim 43, further comprising means for receiving a use command selecting the selected type cardiac events.

45. The system of claim 43, further comprising means for generating the predetermined sequence of pacing parameters based on a measured cardiac timing interval.

* * * * *

UNITED STATES PATENT AND TRADEMARK OFFICE
CERTIFICATE OF CORRECTION

PATENT NO. : 7,123,962 B2  
APPLICATION NO. : 10/307896  
DATED : October 17, 2006  
INVENTOR(S) : Siejko et al.

Page 1 of 1

It is certified that error appears in the above-identified patent and that said Letters Patent is hereby corrected as shown below:

In column 29, line 1, in Claim 37, delete "comprising;" and insert -- comprising: --, therefor.

In column 30, line 4, in Claim 41, delete "furthering" and insert -- further --, therefor.

In column 30, line 33, in Claim 43, delete "cardiophonographic" and insert -- phonocardiographic --, therefor.

Signed and Sealed this

Ninth Day of January, 2007

JON W. DUDAS  
*Director of the United States Patent and Trademark Office*